(12) United States Patent
Contorni

(10) Patent No.: US 8,802,111 B2
(45) Date of Patent: Aug. 12, 2014

(54) MANUFACTURE OF VACCINES THAT CONTAIN BOTH HEPATITIS B VIRUS SURFACE ANTIGENS AND SURFACTANT

(75) Inventor: Mario Contorni, Siena (IT)

(73) Assignee: Novartis Vaccines and Diagnostics, SRL, Siena (IT)

( * ) Notice: Subject to any disclaimer, the term of this patent is extended or adjusted under 35 U.S.C. 154(b) by 0 days.

(21) Appl. No.: 13/302,279

(22) Filed: Nov. 22, 2011

(65) Prior Publication Data

US 2012/0107345 A1    May 3, 2012

Related U.S. Application Data

(63) Continuation of application No. 12/084,753, filed as application No. PCT/IB2006/003662 on Nov. 7, 2006, now abandoned.

(30) Foreign Application Priority Data

Nov. 8, 2005 (GB) .................................. 0522765.7

(51) Int. Cl.
  *A61K 39/29* (2006.01)
  *C07K 14/005* (2006.01)
  *A61K 39/12* (2006.01)
  *C07K 1/26* (2006.01)
  *A61K 39/00* (2006.01)

(52) U.S. Cl.
  CPC ..... *C07K 14/005* (2013.01); *C12N 2730/10134* (2013.01); *A61K 2039/55505* (2013.01); *A61K 39/12* (2013.01); *A61K 39/292* (2013.01); *A61K 39/00* (2013.01); *C12N 2730/10122* (2013.01)
  USPC ..................... 424/227.1; 424/78.26

(58) Field of Classification Search
  None
  See application file for complete search history.

(56) References Cited

U.S. PATENT DOCUMENTS

| | | | |
|---|---|---|---|
| 5,776,468 A | | 7/1998 | Hauser et al. |
| 6,013,264 A | * | 1/2000 | Petre et al. ................. 424/227.1 |
| 8,007,807 B2 | * | 8/2011 | Borkowski ................. 424/184.1 |
| 8,119,146 B2 | * | 2/2012 | Medina-Selby ........... 424/227.1 |
| 2003/0235590 A1 | | 12/2003 | De-Heyder et al. |
| 2011/0311574 A1 | * | 12/2011 | Borkowski ............... 424/196.11 |
| 2013/0004535 A1 | * | 1/2013 | Borkowski ............... 424/197.11 |
| 2013/0004536 A1 | * | 1/2013 | Borkowski ............... 424/197.11 |

FOREIGN PATENT DOCUMENTS

| | | |
|---|---|---|
| EP | 0 414 374 A2 | 2/1991 |
| EP | 1 307 473 B1 | 12/2005 |
| WO | WO 9324148 A * | 12/1993 |
| WO | WO 02/00249 | 1/2002 |
| WO | WO 02/12287 | 2/2002 |
| WO | WO 02/055105 | 7/2002 |
| WO | WO 2006/097851 | 9/2006 |

OTHER PUBLICATIONS

Sigmal-Aldrich, 2013, pp. 1-3. searched by 2013, pp. 1-3.*
"Information for Health Professionals: TRITANRIX-B+HIB," New Zealand Medicines and Medical Services Safety Authority: pp. 1-5 (Oct. 23, 2002).
"EMEA Position Statement: Recent developments concerning thiomersal vaccines," The European Agency of the Evaluation of Medicinal Products (Jun. 29, 2000).
Engerix-B Hepaptitis B Vaccine (recombination) GlaxoSmithKline Biologicals SA (372748392) pp. 1-9 (2009).

* cited by examiner

*Primary Examiner* — Bao Li
(74) *Attorney, Agent, or Firm* — Roberta L. Robins; Robins Law Group

(57) ABSTRACT

When preparing HBsAg for use in a combination vaccine, it us known to add a non-ionic detergent after the HBsAg has been purified. Adding detergents after purification of HBsAg is not optimal, however, as it requires a separate processing step during manufacture. Thus the invention uses them during HBsAg purification.

36 Claims, 6 Drawing Sheets

FIGURE 1
FIGURE 1A
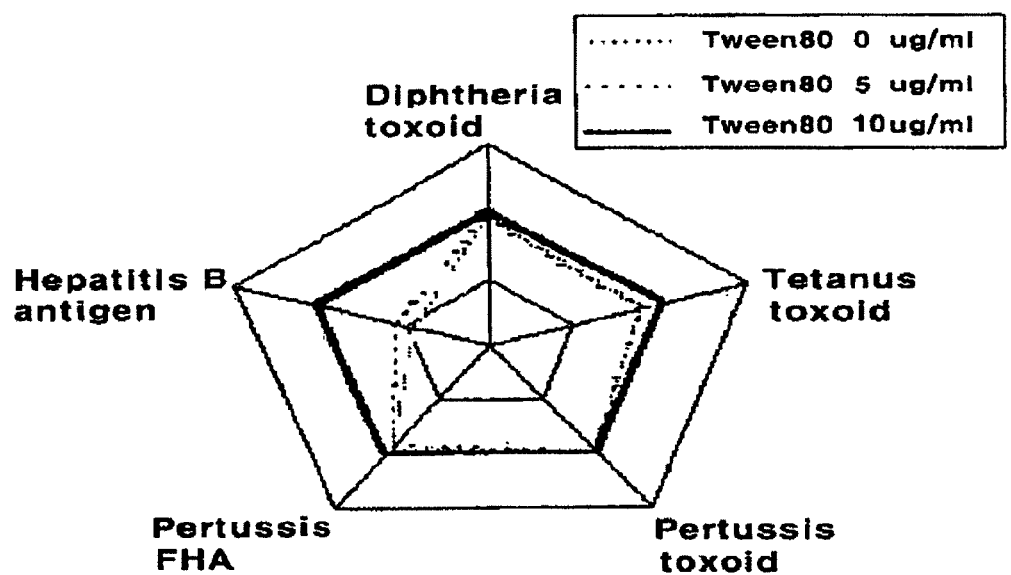
FIGURE 1B
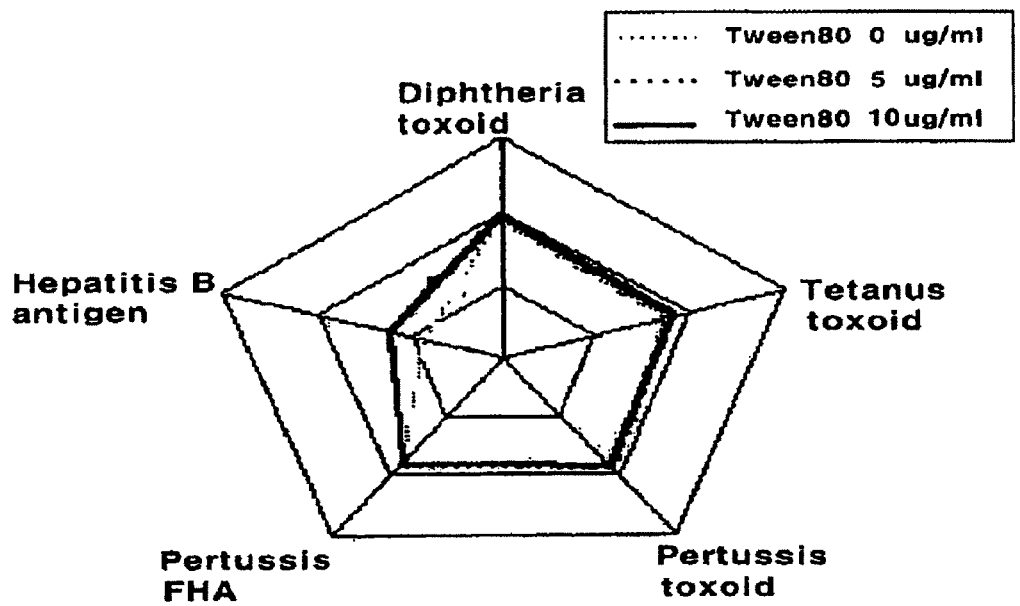

FIGURE 2
FIGURE 2A
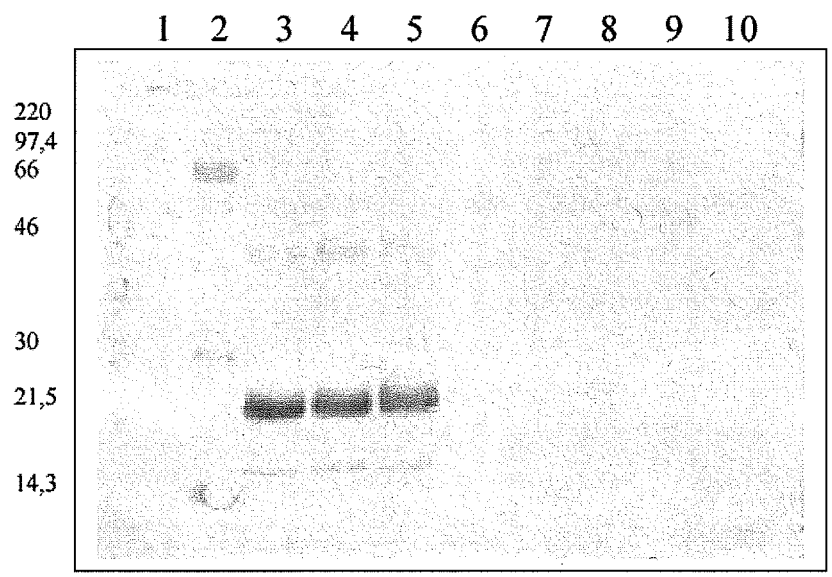
FIGURE 2B
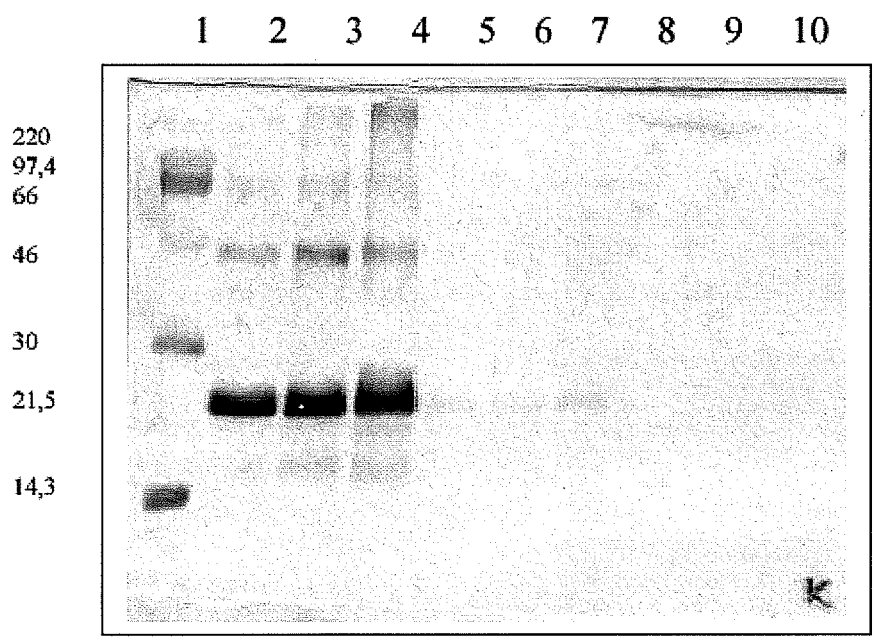

FIGURE 3
FIGURE 3A
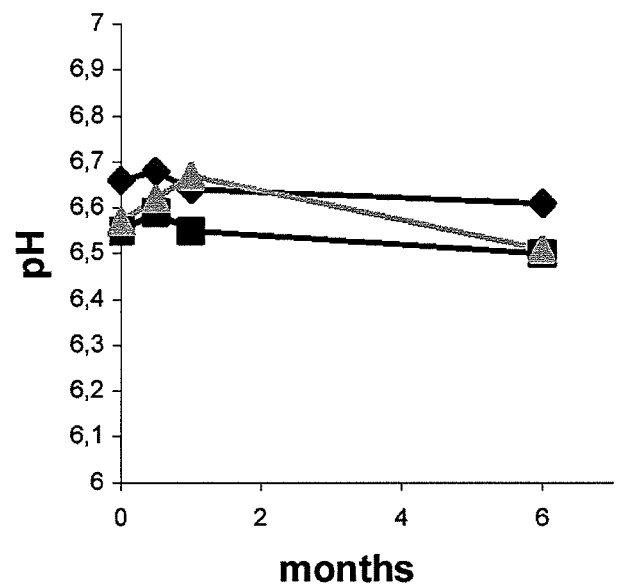
FIGURE 3B
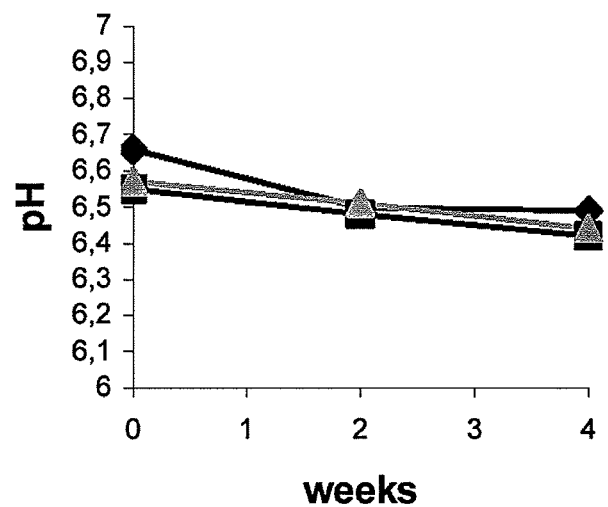

FIGURE 4
FIGURE 4A
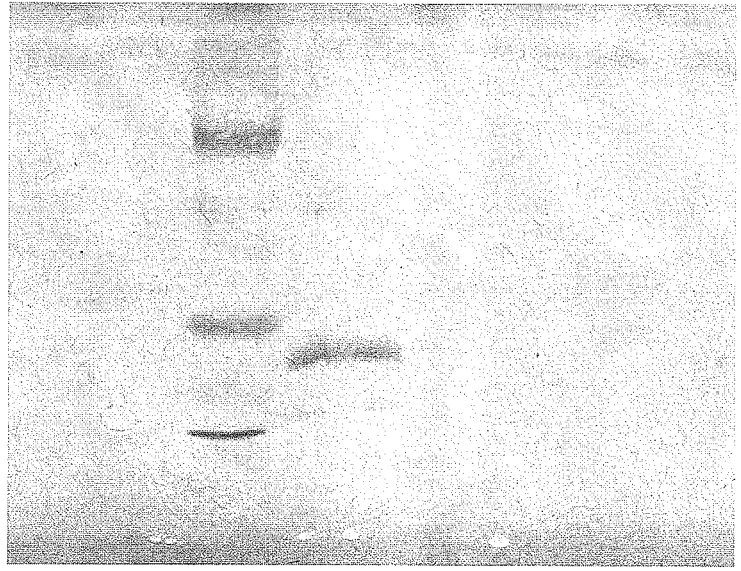
FIGURE 4B
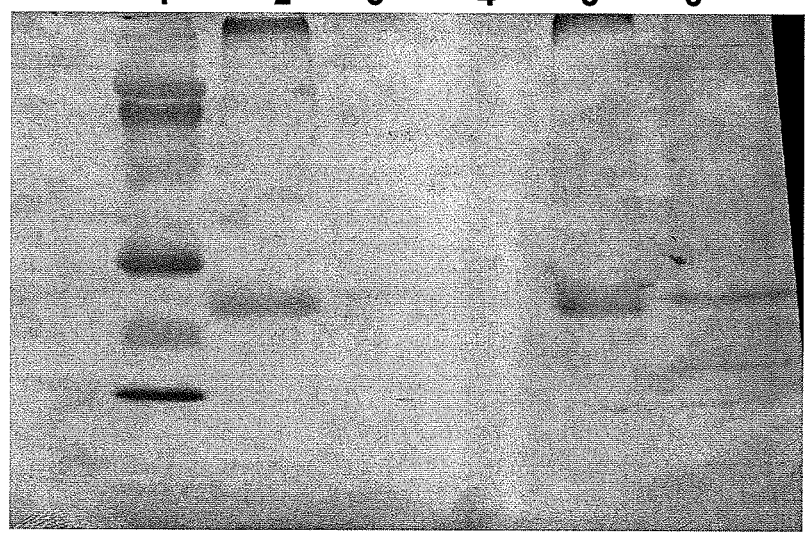

MANUFACTURE OF VACCINES THAT CONTAIN BOTH HEPATITIS B VIRUS SURFACE ANTIGENS AND SURFACTANT

CROSS-REFERENCE TO RELATED APPLICATIONS

This application is a continuation of U.S. patent application Ser. No. 12/084,753, filed Feb. 17, 2009, now abandoned, which is a National Phase filing of International Application No. PCT/IB2006/003662, filed Nov. 7, 2006, which claims the benefit of Great Britain Application No. 0522765.7, filed Nov. 8, 2005, from which applications priority is claimed pursuant to 35 U.S.C. §§119/120. The teachings of the above applications are incorporated herein by reference in their entireties.

All documents cited herein are incorporated by reference in their entireties.

TECHNICAL FIELD

This invention is in the field of manufacturing combination vaccines, that is vaccines containing mixed immunogens from more than one pathogen, such that administration of the vaccine can simultaneously immunize a subject against more than one pathogen. In particular, it concerns the use of surfactants during the manufacture of combination vaccines.

BACKGROUND ART

Vaccines containing antigens from more than one pathogenic organism within a single dose are known as "multivalent" or "combination" vaccines. Various combination vaccines have been approved for human use in the EU and the USA, including trivalent vaccines for protecting against diphtheria, tetanus and pertussis ("DTP" vaccines) and trivalent vaccines for protecting against measles, mumps and rubella ("MMR" vaccines).

Combination vaccines offer patients the advantage of receiving a reduced number of injections, which leads to the clinical advantage of increased compliance (e.g. see chapter 29 of reference 1), particularly for pediatric vaccination. At the same time, however, they present manufacturing difficulties due to factors including: physical and biochemical incompatibility between antigens and other components; immunological interference; and stability.

The inclusion of non-antigen components in vaccines is necessary, but can cause difficulties. Surfactants are a particular problem in combination vaccines because one antigen may require a surfactant for optimal activity, whereas another may be negatively affected by the surfactant's presence. Furthermore, the inclusion of surfactants in pediatric vaccines is of concern to some patient groups, even though the surfactant may be generally accepted as safe.

Of particular interest in the vaccine field are the polyoxyethylene sorbitan esters surfactants, especially the polysorbate 20 (also known as 'Tween 20', or polyoxyethylene sorbitan monolaurate) and polysorbate 80 (also known as 'Tween 80', or polyoxyethylene sorbitan monooleate) species. Polysorbate 20 is found in the monovalent HAVRIX™ inactivated hepatitis A vaccine, and polysorbate 80 is found in combination vaccines such as TRIPEDIA™ and the INFANRIX™ series of vaccines, both of which include diphtheria and tetanus toxoids, and acellular pertussis. These two surfactants have also been used to stabilise liquid rotavirus vaccines [2].

The polysorbates have also been used in the manufacture of combination vaccines that contain hepatitis B surface antigen ('HBsAg') e.g. references 3 & 4 disclose a process for making a tetravalent D-T-P-HBsAg vaccine in which interference with the phospholipid component of the HBsAg is avoided by adding a non-ionic surfactant such as Tween 20, Tween 80 or Triton X-100. The data in FIG. 2 of refs. 3 & 4 (FIG. 1 herein) show that surfactant is required for maintaining HBsAg antigenicity, but is less important for the other components. The highest surfactant concentration tested was 10 µg/ml with 20 µg/ml HBsAg, and this also gave the best antigenicity.

In the process of references 3 and 4, the non-ionic detergent is added after the HBsAg has been purified. Adding detergents after purification of HBsAg is not optimal, however, as it requires a separate processing step during manufacture, which increases the processing time and also increases the risk of introducing contamination into the HBsAg. If a contaminated component is used when making a combination vaccine then the eventual loss is greater than when making monovalent vaccines e.g. if a contaminated HBsAg component is mixed with a clean D-T-P component then the whole D-T-P-HBsAg mixture has to be scrapped, rather than only the HBsAg.

For combination vaccines containing non-ionic surfactants, therefore, there remains a need for a manufacturing processes in which the surfactant does not have to be added as a separate component during the process.

SUMMARY OF THE INVENTION

Rather than adding non-ionic surfactants to antigens after they have been purified [3,4], the invention uses them during antigen purification. This surfactant can thus perform its function in the final combination vaccine, but the risk of contamination (and thus also the risk of loss of a whole combination vaccine after it has been prepared) is reduced.

Thus the invention provides a process for preparing a combination vaccine, wherein the vaccine comprises: (i) a non-ionic surfactant, (ii) a hepatitis B virus (HBV) surface antigen, and (iii) an antigen from at least one non-HBV pathogen, and wherein the process comprises: (i) purifying the HBV surface antigen from recombinant yeast cells, wherein the purification includes a step in which the yeast cells are disrupted in the presence of the non-ionic surfactant, to give a purified HBsAg component; and (ii) combining the purified HBsAg component with at least one further antigen from a non-HBV pathogen, to give the combination vaccine.

To avoid the contamination difficulties described above, the process does not involve a step of adding the non-ionic surfactant as a separate component after HBsAg purification. It is possible for the surfactant (or other surfactants, ionic or non-ionic) to be present in the other antigen components with which the HBsAg is combined to give the combination vaccine, but addition of the surfactant as a separate component on its own is avoided. Thus the surfactant is not added as a separate component to the purified HBsAg component, and it is not added during combination of the antigens.

The invention also provides a process for preparing a combination vaccine, wherein the vaccine comprises: (i) a non-ionic surfactant, (ii) a hepatitis B virus (HBV) surface antigen, and (iii) an antigen from at least one non-HBV pathogen, and wherein the process comprises the step of combining a purified HBV surface antigen with at least one further antigen from a non-HBV pathogen, to give the combination vaccine, wherein the purified HBV surface antigen was prepared by a process in which recombinant HBsAg-expressing yeast cells are disrupted in the presence of the non-ionic surfactant. Again, separate addition of the surfactant is avoided.

The invention also provides an immunogenic composition comprising (i) a non-ionic surfactant, (ii) a hepatitis B virus (HBV) surface antigen, and (iii) an antigen from at least one non-HBV pathogen, wherein the HBV surface antigen was prepared by a process in which recombinant HBsAg-expressing yeast cells were disrupted in the presence of the non-ionic surfactant. Again, the HBsAg was prepared while avoiding separate addition of the surfactant. This product may be distinguished from products where HBsAg was prepared by a different process because the non-ionic surfactant used during purification can be retained within a HBsAg particle.

The Non-Ionic Surfactant

The invention can utilise a variety of non-ionic surfactants [5], and particularly those that are found in vaccine formulations. Organic surfactants are preferred. These are typically the reaction product of an alkylene oxide (e.g. ethylene oxide) with a fatty alcohol, fatty acid, alkylphenol, alkylamine or other appropriate compound having at least one active hydrogen atom. For most surfactants the most common alcohols, amines and acids have a carbon chain length in the range $C_8$-$C_{18}$. The most common alkylphenols are nonylphenol and octylphenol. Surfactants containing poly(oxyethene) residues are particularly preferred.

For example, the invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); polyoxyethylene fatty ethers derived from lauryl, cetyl, stearyl and oleyl alcohols (known as Brij surfactants), such as triethyleneglycol monolauryl ether (Brij 30); and sorbitan esters (commonly referred to as the SPANs), such as sorbitan trioleate (Span 85) and sorbitan monolaurate.

The invention is particularly suitable for use with polysorbate 20. This surfactant has an established safety profile for administration to humans, including within vaccines.

Surfactants can be classified by their 'HLB' (hydrophile/lipophile balance). Preferred surfactants of the invention have a HLB of at least 10, preferably at least 15, and more preferably at least 16. The non-ionic surfactant is a component of compositions of the invention. To avoid administering large doses of the surfactant to a patient, it is preferred that the concentration of the surfactant in the composition should be no more than 30 µg/ml e.g. ≤25 µg/ml, ≤20 µg/ml, ≤15 µg/ml, ≤10 µg/ml, ≤5 µg/ml, etc. A concentration of ≤10 µg/ml is preferred.

As an alternative to specifying a concentration of surfactant, it is preferred that the amount of the surfactant in the composition should be less than 50 µg (e.g. ≤40 µg, ≤30 µg, ≤25 µg, ≤20 µg, ≤15 µg, ≤10 µg, etc.) for every 100 µg of HBsAg. References 3 & 4 similarly suggest a surfactant:HBsAg mass ratio of less than 50%. Less than 25 µg of the surfactant per 100 µg HBsAg is preferred.

As mentioned in more detail below, preferred processes of the invention utilise a pre-mixed component including diphtheria and tetanus toxoids. This D-T component is preferably substantially free from non-ionic surfactants, and in particular is free from polysorbates 20 and 80. Similarly, a pre-mixed D-T-Pw component is free from non-ionic surfactants e.g. polysorbates 20 and 80.

The Hepatitis B Virus Surface Antigen

Hepatitis B virus (HBV) is one of the known agents which causes viral hepatitis. The HBV virion consists of an inner core surrounded by an outer protein coat or capsid, and the viral core contains the viral DNA genome. The major component of the capsid is a protein known as HBV surface antigen or, more commonly, 'HBsAg', which is typically a 226-amino acid polypeptide with a molecular weight of ~24 kDa. All existing hepatitis B vaccines contain HBsAg, and when this antigen is administered to a normal vaccinee it stimulates the production of anti-HBsAg antibodies which protect against HBV infection.

For vaccine manufacture, HBsAg can be made in two ways. The first method involves purifying the antigen in particulate form from the plasma of chronic hepatitis B carriers, as large quantities of HBsAg are synthesized in the liver and released into the blood stream during an HBV infection. The second way involves expressing the protein by recombinant DNA methods. HBsAg for use with the method of the invention is recombinantly expressed in yeast cells. Suitable yeasts include *Saccharomyces* (such as *S. cerevisiae*) or *Hanensula* (such as *H. polymorpha*) hosts.

Unlike native HBsAg (i.e. as in the plasma-purified product), yeast-expressed HBsAg is generally non-glycosylated, and this is the most preferred form of HBsAg for use with the invention. Yeast-expressed HBsAg is highly immunogenic and can be prepared without the risk of blood product contamination.

The HBsAg will generally be in the form of substantially-spherical particles (average diameter of about 20 nm), including a lipid matrix comprising phospholipids. Yeast-expressed HBsAg particles may include phosphatidylinositol, which is not found in natural HBV virions. The particles may also include a non-toxic amount of LPS in order to stimulate the immune system [6].

The HBsAg is preferably from HBV subtype adw2.

Many methods for purifying HBsAg are known in the art (e.g. see refs 7-33. These methods are disclosed for use in making monovalent HBsAg preparations but, unlike the method disclosed in references 3 and 4, none of them relates to the purification of HBsAg specifically for use in combination vaccines. Any of these and other processes can be used, provided that the process is suitable for purifying the antigen after expression in recombinant yeast cells, wherein the purification includes a step in which the yeast cells are disrupted in the presence of the non-ionic surfactant.

A preferred method for HBsAg purification involves, after cell disruption: ultrafiltration; size exclusion chromatography; anion exchange chromatography; ultracentrifugation; desalting; and sterile filtration. Lysates may be precipitated after cell disruption (e.g. using a polyethylene glycol), leaving HBsAg in solution, ready for ultrafiltration.

After purification HBsAg may be subjected to dialysis (e.g. with cysteine), which can be used to remove any mercurial preservatives such as thimerosal that may have been used during HBsAg preparation [30,34].

Quantities of HBsAg are typically expressed in micrograms, and a typical amount of HBsAg per vaccine dose is 10 µg.

In addition to the 'S' sequence, a surface antigen may include all or part of a pre-S sequence, such as all or part of a pre-S1 and/or pre-S2 sequence.

The Non-HBV Antigens

Immunogenic compositions of the invention include at least one protective antigen from at least one non-HBV pathogen. The non-HBV pathogen(s) can be viral and/or bacterial.

Typical viral pathogens include, but are not limited to: poliovirus; hepatitis A virus; influenza virus; measles virus; mumps virus; rubella virus; and varicella zoster virus.

Typical bacterial pathogens include, but are not limited to: *Corynebacterium diphtheriae*; *Clostridium tetani*; *Bordetella pertussis*; *Haemophilus influenzae*, including type b and non-typeable strains; *Neisseria meningitidis*, including serogroups A, B, C, W135 and/or Y; *Streptococcus pneumoniae*, including serotypes 4, 6B, 9V, 14, 18C, 19F, and 23F; and *Moraxella catarrhalis*.

*Corynebacterium diphtheriae* causes diphtheria. Diphtheria toxin can be treated (e.g. using formalin or formaldehyde) to remove toxicity while retaining the ability to induce specific anti-toxin antibodies after injection. These diphtheria toxoids are used in diphtheria vaccines, and are disclosed in more detail in chapter 13 of reference 1. Preferred diphtheria toxoids are those prepared by formaldehyde treatment. The diphtheria toxoid can be obtained by growing *C. diphtheriae* in growth medium (e.g. Fenton medium, or Linggoud & Fenton medium), which may be supplemented with bovine extract, followed by formaldehyde treatment, ultrafiltration and precipitation. The toxoided material may then be treated by a process comprising sterile filtration and/or dialysis.

*Clostridium tetani* causes tetanus. Tetanus toxin can be treated to give a protective toxoid. The toxoids are used in tetanus vaccines, and are disclosed in more detail in chapter 27 of reference 1. Preferred tetanus toxoids are those prepared by formaldehyde treatment. The tetanus toxoid can be obtained by growing *C. tetani* in growth medium (e.g. a Latham medium derived from bovine casein), followed by formaldehyde treatment, ultrafiltration and precipitation. The material may then be treated by a process comprising sterile filtration and/or dialysis.

*Bordetella pertussis* causes whooping cough. Pertussis antigens in vaccines are either cellular (whole cell, in the form of inactivated *B. pertussis* cells; 'wP') or acellular ('aP'). Preparation of cellular pertussis antigens is well documented [e.g. see chapter 21 of reference 1] e.g. it may be obtained by heat inactivation of phase I culture of *B. pertussis*. Where acellular antigens are used, one, two or (preferably) three of the following antigens are included: (1) detoxified pertussis toxin (pertussis toxoid, or 'PT'); (2) filamentous hemagglutinin ('FHA'); (3) pertactin (also known as the '69 kiloDalton outer membrane protein'). These three antigens are preferably prepared by isolation from *B. pertussis* culture grown in modified Stainer-Scholte liquid medium. PT and FHA can be isolated from the fermentation broth (e.g. by adsorption on hydroxyapatite gel), whereas pertactin can be extracted from the cells by heat treatment and flocculation (e.g. using barium chloride). The antigens can be purified in successive chromatographic and/or precipitation steps. PT and FHA can be purified by hydrophobic chromatography, affinity chromatography and size exclusion chromatography. Pertactin can be purified by ion exchange chromatography, hydrophobic chromatography and size exclusion chromatography. FHA and pertactin may be treated with formaldehyde prior to use according to the invention. PT is preferably detoxified by treatment with formaldehyde and/or glutaraldehyde. As an alternative to this chemical detoxification procedure the PT may be a mutant PT in which enzymatic activity has been reduced by mutagenesis [35], but detoxification by chemical treatment is preferred. *Haemophilus influenzae* type b ('Hib') causes bacterial meningitis. Hib vaccines are typically based on the capsular saccharide antigen [e.g. chapter 14 of ref 1], the preparation of which is well documented [e.g. references 36 to 45]. The Hib saccharide is conjugated to a carrier protein in order to enhance its immunogenicity, especially in children. Typical carrier proteins are tetanus toxoid, diphtheria toxoid, the CRM197 derivative of diphtheria toxoid, *H. influenzae* protein D, and an outer membrane protein complex from serogroup *B meningococcus*. Tetanus toxoid is the preferred carrier, as used in the product commonly referred to as 'PRP-T'. PRP-T can be made by activating a Hib capsular polysaccharide using cyanogen bromide, coupling the activated saccharide to an adipic acid linker (such as (1-ethyl-3-(3-dimethylaminopropyl) carbodiimide), typically the hydrochloride salt), and then reacting the linker-saccharide entity with a tetanus toxoid carrier protein. The saccharide moiety of the conjugate may comprise full-length polyribosylribitol phosphate (PRP) as prepared from Hib bacteria, and/or fragments of full-length PRP. Conjugates with a saccharide:protein ratio (w/w) of between 1:5 (i.e. excess protein) and 5:1 (i.e. excess saccharide) may be used e.g. ratios between 1:2 and 5:1 and ratios between 1:1.25 and 1:2.5. In preferred vaccines, however, the weight ratio of saccharide to carrier protein is between 1:2.5 and 1:3.5. In vaccines where tetanus toxoid is present both as an antigen and as a carrier protein then the weight ratio of saccharide to carrier protein in the conjugate may be between 1:0.3 and 1:2 [46]. Administration of the Hib conjugate preferably results in an anti-PRP antibody concentration of $\geq 0.15$ µg/ml, and more preferably $\geq 1$ µg/ml, and these are the standard response thresholds.

*Neisseria meningitidis* causes bacterial meningitis. Based on the organism's capsular polysaccharide, various serogroups of *N. meningitidis* have been identified, including A, B, C, H, I, K, L, 29E, W135, X, Y & Z. The serogroups most associated with disease are A, B, C, W135 and Y. Current vaccines against serogroups A, C, W135 and Y are based on the capsular saccharide antigens, but this approach is not suitable for serogroup B, and so protein antigens and outer-membrane vesicles are used instead. The capsular saccharides are conjugated to carrier proteins in order to enhance immunogenicity. Typical carrier proteins are tetanus toxoid, diphtheria toxoid, the CRM197 derivative of diphtheria toxoid, and *H. influenzae* protein D. The saccharide moiety of the conjugate may comprise full-length saccharide as prepared from meningococci, and/or fragments thereof. Serogroup C saccharides may be prepared from either OAc+ or OAc− strains. For serogroup A saccharides, preferably at least 50% (e.g. at least 60%, 70%, 80%, 90%, 95% or more) of the mannosamine residues are O-acetylated at the C-3 position. Meningococcal conjugates with a saccharide:protein ratio (w/w) of between 1:10 (i.e. excess protein) and 10:1 (i.e. excess saccharide) may be used e.g. ratios between 1:5 and 5:1, between 1:2.5 and 2.5:1, or between 1:1.25 and 1.25:1. Administration of a conjugate preferably results in an increase in serum bactericidal assay (SBA) titre for the relevant serogroup of at least 4-fold, and preferably at least 8-fold. SBA titres can be measured using baby rabbit complement or human complement [47].

*Streptococcus pneumoniae* causes bacterial meningitis. As for Hib and meningococcus, existing vaccines are based on capsular saccharides. It is preferred to include saccharides from more than one serotype of *S. pneumoniae*, and particularly at least serotypes 6B, 14, 19F and 23F. Further serotypes are preferably selected from: 1, 3, 4, 5, 7F, 9V and 18C. For example, mixtures of polysaccharides from 23 different serotype are widely used, as are conjugate vaccines with polysaccharides from between 5 and 11 different serotypes [48]. For example, PrevNar™ [49] contains conjugated antigens from seven serotypes (4, 6B, 9V, 14, 18C, 19F, and 23F). Saccharides are preferably conjugated to carrier proteins [e.g. refs. 50 to 52]. Typical carrier proteins are tetanus toxoid, diphtheria toxoid, the CRM197 derivative of diphtheria toxoid, and *H. influenzae* protein D. Saccharides in the PrevNar™ product are individually conjugated to CRM197 by reductive amination, with 2 μg of each saccharide per 0.5 ml dose (4 μg of serotype 6B). As an alternative to using saccharide antigens from pneumococcus, the composition may include one or more polypeptide antigens. Genome sequences for several strains of pneumococcus are available [53,54] and can be subjected to reverse vaccinology [55-58] to identify suitable polypeptide antigens [59,60]. For example, the composition may include one or more of the following antigens: PhtA, PhtD, PhtB, PhtE, SpsA, LytB, LytC, LytA, Sp125, Sp101, Sp128, Sp130 and Sp130, as defined in reference 61. The composition may include more than one (e.g. 2, 3, 4, 5, 6, 7, 8, 9 10, 11, 12, 13 or 14) of these antigens. In some embodiments, the composition may include both saccharide and polypeptide antigens from pneumococcus. These may be used in simple admixture, or the pneumococcal saccharide antigen may be conjugated to a pneumococcal protein. Suitable carrier proteins for such embodiments include the pneumococcal protein antigens listed above [61].

*Moraxella catarrhalis* causes otitis media and sinusitis, and is an occasional cause of laryngitis. Vaccines are currently under investigation, as reviewed in reference 62.

Like HBV, HAV causes hepatitis. HAV vaccines are disclosed in chapter 15 of reference 1. A preferred HAV component is based on inactivated virus, and inactivation can be achieved by formalin treatment. Virus can be grown on human embryonic lung diploid fibroblasts, such as MRC-5 cells. A preferred HAV strain is HM175, although CR326F can also be used. The cells can be grown under conditions that permit viral growth. The cells are lysed, and the resulting suspension can be purified by ultrafiltration and gel permeation chromatography.

Poliovirus causes poliomyelitis. Rather than use oral poliovirus vaccine, the invention uses inactivated polio virus vaccine (IPV), as disclosed in more detail in chapter 24 of reference 1. Polioviruses may be grown in cell culture, and a preferred culture uses a Vero cell line, derived from monkey kidney. Vero cells can conveniently be cultured microcarriers. After growth, virions may be purified using techniques such as ultrafiltration, diafiltration, and chromatography. Prior to administration to patients, polioviruses must be inactivated, and this can be achieved by treatment with formaldehyde. Poliomyelitis can be caused by one of three types of poliovirus. The three types are similar and cause identical symptoms, but they are antigenically very different and infection by one type does not protect against infection by others. It is therefore preferred to use three poliovirus antigens in the invention: poliovirus Type 1 (e.g. Mahoney strain), poliovirus Type 2 (e.g. MEF-1 strain), and poliovirus Type 3 (e.g. Saukett strain). The viruses are preferably grown, purified and inactivated individually, and are then combined to give a bulk trivalent mixture for use with the invention. Quantities of IPV are typically expressed in the 'DU' unit (the "D-antigen unit" [63]).

Antigens for protecting against measles, mumps and rubella viruses are typically live viruses, as found in known monovalent and trivalent ('MMR') vaccines. Measles virus vaccines are described in more detail in chapter 19 of reference 1. Mumps virus vaccines are described in more detail in chapter 20 of reference 1. Rubella virus vaccines are described in more detail in chapter 26 of reference 1. Typical measles virus strains include: Moraten; Connaught; Schwarz; Edmonston-Zagreb; CAM-70; AIK-C; TD97; Leningrad-16; Shanghai-191; etc. The Schwarz and Moraten strains are most common for use in USA and Europe. Typical mumps virus strains include: Jeryl Lynn; RIT 4385; Urabe; Hoshino; Rubini; Leningrad-3; Leningrad-Zagreb; Miyahara; Torii; NK M-46; 5-12; etc. The Jeryl Lynn, RIT 4385, Urabe and Leningrad-Zagreb strains are the most common worldwide strains. Typical rubella virus strains include: RA27/3; Matsuba; TCRB 19; Takahashi; Matsuura; TP-336; etc. RA27/3 is the most common strain used in the western world.

VZV antigens for protecting against chickenpox are typically live viruses, based on the Oka strain of the virus. VZV vaccines are described in more detail in chapter 28 of reference 1. Influenza virus antigens are described in more detail in chapters 17 & 18 of reference 1. Broadly, influenza virus vaccines can be based on live virus or inactivated virus, and inactivated vaccines can be based on whole virus, 'split' virus or on purified surface antigens (including hemagglutinin and neuraminidase). The viruses used to prepare the vaccines can be grown either on eggs or on cell culture. Vaccine strains for influenza virus change from season to season. In the current inter-pandemic period, vaccines typically include two influenza A strains (H1N1 and H3N2) and one influenza B strain, and trivalent vaccines are typical. The invention may also use viruses from pandemic strains (i.e. strains to which the vaccine recipient and the general human population are immunologically naïve), such as H2, H5, H7 or H9 subtype strains (in particular of influenza A virus), and influenza vaccines for pandemic strains may be monovalent or may be based on a normal trivalent vaccine supplemented by a pandemic strain. The influenza virus may be a reassortant strain, and may have been obtained by reverse genetics techniques. The virus may be attenuated. The virus may be temperature-sensitive. The virus may be cold-adapted. Antigenic components from these pathogens for use in vaccines are commonly referred to by abbreviated names: 'D' for diphtheria toxoid; 'T' for tetanus toxoid; 'P' for pertussis antigens, with 'Pa' being acellular and 'Pw' being cellular; 'Hib' for *H. influenzae* b capsular saccharide; 'MenA', 'MenB', 'MenC', 'MenW' and 'MenY' for the respective meningococcal serogroups; 'IPV' for inactivated poliovirus; and 'Spn' for pneumococcus.

When combining antigenic components with HBsAg to prepare a multivalent composition, the antigens can be added individually, or they can be pre-mixed before being combined with HBsAg. Where D and T antigens are used, it is preferred to use a pre-mixed D-T component. This bivalent component can be used in the processes of the invention e.g. it can be combined with HBsAg to make a trivalent D-T-HBV component. As an alternative, the D-T component can be combined with further non-HBV antigens (e.g. with acellular pertussis antigens), and that component can then be combined with HBsAg, etc. Where D, T and Pw antigens are used, it is preferred to use a pre-mixed D-T-Pw component, and then to use this component during the processes of the invention.

When an adjuvant is included in the compositions of the invention, this also can be added at various stages. Typically, antigens will have been combined with adjuvants before being used in the processes of the invention (e.g. a bivalent D-T mixture will have been adsorbed to aluminium salt adjuvant(s) before being used in the processes of the invention, which can be conveniently be achieved by preparing the toxoids separately, adsorbing each of them separately to an aluminium hydroxide adjuvant, and then mixing the two adsorbed toxoids (optionally with further adjuvant) to give the material for use in the process of the invention), but it is also possible to add adjuvant after the antigens have been mixed, or to add the antigens to an adjuvant (e.g. to start with an aqueous adjuvant, then to add antigens, either individually or pre-mixed). As described below, the HBsAg component is preferably adsorbed to an aluminium phosphate adjuvant before being combined with the non-HBV antigenic components.

Preferred compositions of the invention include at least D, T and P antigens (cf. refs. 3 & 4) in addition to the HBsAg. Particularly preferred compositions are the following combinations:

HBsAg, D, T
HBsAg, D, T, Pw.
HBsAg, D, T, Pw, Hib.
HBsAg, D, T, Pw, Hib, MenA, MenC.
HBsAg, D, T, Pw, Hib, MenA, MenC, MenW135.
HBsAg, D, T, Pw, Hib, MenA, MenC, MenY.
HBsAg, D, T, Pw, Hib, MenA, MenC, MenW135, MenY.
HBsAg, D, T, Pa.
HBsAg, D, T, Pa, Hib
HBsAg, D, T, Pa, poliovirus.
HBsAg, D, T, Pa, poliovirus, Hib.
HBsAg, D, T, Pa, poliovirus, Hib, MenC.
HBsAg, D, T, Pa, poliovirus, Hib, MenC, MenA.
HBsAg, D, T, Pa, poliovirus, Hib, MenC, MenY.
HBsAg, D, T, Pa, poliovirus, Hib, MenC, MenW135.
HBsAg, D, T, Pa, poliovirus, Hib, MenC, MenA, MenW135, MenY.
HBsAg, Hib
HBsAg, hepatitis A virus.

These compositions may consist of the antigens listed, or may further include antigens from additional pathogens. Thus they can be used separately, or as components of further vaccines. In some embodiments of the invention, the composition is not a 5-valent D-T-Pa-HBV-IPV [30]. Thus the composition may include a Pw component and/or at least one conjugate.

Adjuvants

Preferred immunogenic compositions of the invention include an adjuvant, and this adjuvant preferably comprises one or more aluminium salts, and particularly an aluminium phosphate adjuvant and/or an aluminium hydroxide adjuvant.

Antigenic components used in the processes of the invention preferably include aluminium adjuvants before being used in the process i.e. they are 'pre-mixed' or 'pre-adsorbed' to the adjuvant(s).

In compositions comprising HBsAg and a diphtheria toxoid, the diphtheria toxoid may be adsorbed onto an aluminium hydroxide adjuvant.

In compositions comprising HBsAg and a tetanus toxoid, the tetanus toxoid may be adsorbed onto an aluminium hydroxide adjuvant, but this is not necessary (e.g. adsorption of between 0-10% of the total tetanus toxoid can be used).

In compositions comprising HBsAg and a whole-cell pertussis antigen, the wP antigen is preferably combined with an aluminium hydroxide adjuvant and/or an aluminium phosphate adjuvant.

In compositions comprising HBsAg and acellular pertussis antigen(s), the pertussis antigen(s) may be adsorbed onto one or more an aluminium salt adjuvants, or may be added in an unadsorbed state. Where pertactin is present in a composition then it is preferably adsorbed onto an aluminium hydroxide adjuvant before being used in the process of the invention. PT and FHA may be adsorbed onto an aluminium hydroxide adjuvant or an aluminium phosphate adjuvant before being used in the process of the invention. In preferred embodiments, PT, FHA and pertactin are separately pre-adsorbed to aluminium hydroxide prior to being used in the process of the invention.

In compositions comprising HBsAg and Hib antigens, the Hib conjugate may be unadsorbed, but it is preferably adsorbed to an aluminium phosphate adjuvant [64]. Adsorption in this way is particularly useful in vaccines comprising D-T-Pw-Hib-HBsAg antigens. Other conjugated antigens (e.g. meningococcus, pneumococcus) can similarly be adsorbed to an aluminium salt (e.g. a phosphate) or can be unadsorbed [65].

IPV antigens are typically not adsorbed to any adjuvant before being used in a process of the invention, but they can become adsorbed onto aluminium adjuvant(s) originating with other components.

The HBsAg in the composition can be adsorbed onto aluminium phosphate using the methods described in ref. 66. Adsorption to aluminium phosphate contrasts with the well-known ENGERIX-B™ product (recombinant hepatitis B vaccine where HBsAg is adsorbed to aluminium hydroxide), but is the same as in the HEPACCINE™ (containing heat inactivated HBsAg) and RECOMBIVAX™ (containing recombinant HBsAg) products. As mentioned in reference 67, aluminium phosphate can be a better adjuvant for HBsAg than aluminium hydroxide. Although HBsAg may be adsorbed to an aluminium hydroxide adjuvant in the final vaccine (as in the well-known ENGERIX-B™ product), or may remain unadsorbed, it will generally be adsorbed to an aluminium phosphate adjuvant. Moreover, it is preferably pre-adsorbed to the aluminium phosphate prior to being used in the process of the invention.

Where a process of the invention utilises a component in which diphtheria and tetanus toxoids have been mixed prior to their being combined with HBsAg, this D-T mixture preferably contains an aluminium hydroxide adjuvant, to which the D and T antigens are adsorbed.

Where a process of the invention utilises a component in which diphtheria toxoid, tetanus toxoid and whole-cell pertussis antigen have been mixed prior to their being combined with HBsAg, this D-T-Pw mixture preferably contains both an aluminium hydroxide adjuvant, to which the D and T antigens are adsorbed, and an aluminium phosphate adjuvant.

Aluminium adjuvants currently in use are typically referred to either as "aluminium hydroxide" or as "aluminium phosphate" adjuvants. These are names of convenience, however, as neither is a precise description of the actual chemical compound which is present (e.g. see chapter 9 of reference 68). The invention can use any of the "hydroxide" or "phosphate" salts that are in general use as adjuvants.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide Al(OH)$_3$, by infrared (IR) spectroscopy, in particular by the presence of an adsorption band at 1070 cm$^{-1}$ and a strong shoulder at 3090-3100 cm$^{-1}$ (chapter 9 of ref. 68).

The adjuvants known as "aluminium phosphate" are typically aluminium hydroxyphosphates, often also containing a small amount of sulfate. They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 0.99. Hydroxyphosphates can be distinguished from strict AlPO$_4$ by the presence of hydroxyl groups. For example, an IR spectrum band at 3164 cm$^{-1}$ (e.g. when heated to 200° C.) indicates the presence of structural hydroxyls (chapter 9 of ref. 68).

The $PO_4/Al^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4/Al$ molar ratio between 0.84 and 0.92, included at 0.6 mg $Al^{3+}$/ml. The aluminium phosphate will generally be particulate. Typical diameters of the particles are in the range 0.5-20 μm (e.g. about 5-10 μm) after any antigen adsorption.

The PZC of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

An aluminium phosphate solution used to prepare a composition of the invention may contain a buffer (e.g. a phosphate or a histidine or a Tris buffer), but this is not always necessary. The aluminium phosphate solution is preferably sterile and pyrogen-free. The aluminium phosphate solution may include free aqueous phosphate ions e.g. present at a concentration between 1.0 and 20 mM, preferably between 5 and 15 mM, and more preferably about 10 mM. The aluminium phosphate solution may also comprise sodium chloride. The concentration of sodium chloride is preferably in the range of 0.1 to 100 mg/ml (e.g. 0.5-50 mg/ml, 1-20 mg/ml, 2-10 mg/ml) and is more preferably about 3±1 mg/ml. The presence of NaCl facilitates the correct measurement of pH prior to adsorption of antigens.

In some embodiments, the invention may exclude compositions that comprise an oil-in-water emulsion containing a mixture of polysorbate 80, Span 85 and squalene [69]. In some embodiments, the invention may exclude compositions that comprise a mixture of an oil, an α-tocopherol and polysorbate 80 [70]. In some embodiments, the invention may exclude compositions that comprise a saponin adjuvant (such as QS21) and a non-ionic surfactant (such as polysorbate 40, 60 or 80). In some embodiments, the invention may exclude compositions that comprise a saponin adjuvant, a metabolisable oil and a non-ionic surfactant [71]. In some embodiments, the invention may exclude compositions that comprise a saponin adjuvant, an oil-in-water emulsion and a sterol [72]. In some embodiments, the invention may exclude compositions that comprise 3d-MPL, QS21, a triglyceride and an oil-in-water emulsion [73].

Combining Purified HBsAg with Further Antigen(s)

The processes of the invention include a step in which purified HBsAg is combined with at least one antigen from at least one non-HBV pathogen.

Antigens can be combined individually in series, or they can be pre-mixed and added together. For example, a 4-valent DTP-HBsAg vaccine can be made by a process involving serial addition of HBsAg, D, T and P antigens to a vessel, or by pre-mixing D, T and P antigens and then combining the HBsAg and the DTP mixture.

Antigenic components can be combined in any suitable order.

The antigen(s) from non-HBV pathogen(s) may comprise a surfactant, and this can be the same as or different from the non-ionic surfactant used during HBsAg purification. The processes of the invention are particularly useful where the other antigenic component(s) comprise a surfactant, as multiple separate steps for surfactant addition are avoided. Processes in which one or more of the non-HBV components comprise polysorbate 80 are preferred.

Where diphtheria and tetanus toxoids are included in a composition of the invention, they are preferably pre-mixed before being combined with HBsAg. Thus the process of the invention involves combining a first component comprising HBsAg with a second component comprising both D and T antigens. Similarly, where diphtheria toxoid, tetanus toxoid and whole cell pertussis antigens are included in a composition, they are preferably pre-mixed, and so the process of the invention involves combining a first component comprising HBsAg with a second component comprising D, T and Pw antigens.

Where a D-T mixture is used, the ratio of diphtheria toxoid to tetanus toxoid in vaccines of the invention is usually between 2:1 and 3:1 (measured in Lf units), preferably between 2.4:1 and 2.6:1, and is more preferably 2.5:1.

When an adjuvant is included in the compositions of the invention, this also can be added at various stages. Typically, antigens will have been combined with adjuvants before being used in the processes of the invention (e.g. a bivalent D-T mixture will have been adsorbed to aluminium salt adjuvant(s) before being used in the processes of the invention), but it is also possible to add adjuvant after the antigens have been mixed, or to add the antigens to an adjuvant (e.g. to start with an aqueous adjuvant, then to add antigens, either individually or pre-mixed). As described above, the HBsAg component may be adsorbed to an aluminium phosphate adjuvant before being combined with the non-HBV antigenic components.

The Combination Vaccine

Compositions of the invention may comprise: (a) an antigenic component; and (b) a non-antigenic component. The antigenic component can comprise or consist of the antigens disclosed above. The non-antigenic component can include carriers, adjuvants, excipients, buffers, etc., as described in more detail below. These non-antigenic components may have various sources. For example, they may be present in one of the antigen or adjuvant materials that is used during manufacture or may be added separately from those components.

Preferred compositions of the invention include one or more pharmaceutical carrier(s) and/or excipient(s).

To control tonicity, it is preferred to include a physiological salt, such as a sodium salt. Sodium chloride (NaCl) is preferred, which may be present at between 1 and 20 mg/ml.

Compositions will generally have an osmolality of between 200 mOsm/kg and 400 mOsm/kg, preferably between 240-360 mOsm/kg, and will more preferably fall within the range of 280-320 mOsm/kg. Osmolality has previously been reported not to have an impact on pain caused by vaccination [74], but keeping osmolality in this range is nevertheless preferred.

Compositions of the invention may include one or more buffers. Typical buffers include: a phosphate buffer; a Tris buffer; a borate buffer; a succinate buffer; a histidine buffer; or a citrate buffer. Buffers will typically be included in the 5-20 mM range.

The pH of a composition of the invention will generally be between 5.0 and 7.5, and more typically between 5.0 and 6.0 for optimum stability or, where a diphtheria toxoid and/or tetanus toxoid is present, between 6.0 and 7.0. The process of the invention may therefore include a step of adjusting the pH of the bulk vaccine prior to packaging.

Compositions of the invention are preferably sterile.

Compositions of the invention are preferably non-pyrogenic e.g. containing <1 EU (endotoxin unit, a standard measure) per dose, and preferably <0.1 EU per dose.

Compositions of the invention are preferably gluten free.

Due to the adsorbed nature of the HBsAg, the final vaccine product may be a suspension with a cloudy appearance. This appearance means that microbial contamination is not readily visible, and so the vaccine preferably contains an antimicrobial agent. This is particularly important when the vaccine is packaged in multidose containers. Preferred antimicrobials for inclusion are 2-phenoxyethanol and thimerosal. It is preferred, however, not to use mercurial preservatives (e.g. thimerosal) during the process of the invention. Thus, between 1 and all of the components used in the process may be substantially free from mercurial preservative (particularly: a bivalent D-T component; an IPV component; a conjugate component). However, the presence of trace amounts may be unavoidable if a component (particularly HBsAg) was treated with such a preservative before being used in the invention. For safety, however, it is preferred that the final composition contains less than about 25 ng/ml mercury. More preferably, the final vaccine product contains no detectable thimerosal. This will generally be achieved by removing the mercurial preservative from an antigen preparation prior to its addition in the process of the invention or by avoiding the use of thimerosal during the preparation of the components used to make the composition.

Where a bivalent D-T mixture is used during a process of the invention, it should be free from thimerosal. In some embodiments, the D-T mixture may include 2-phenoxyethanol, but in others it is free from both thimerosal and 2-phenoxyethanol. Where a trivalent D-T-Pw mixture is used during a process of the invention, it can be free from 2-phenoxyethanol, but may include thimerosal.

During manufacture, dilution of components to give desired final concentrations will usually be performed with WFI (water for injection).

The concentration of aluminium phosphate in a composition of the invention, expressed in terms of $Al^{3+}$, is preferably less than 5 mg/ml e.g. ≤4 mg/ml, ≤3 mg/ml, ≤2 mg/ml, ≤1 mg/ml, etc.

The concentration of HBsAg in a composition of the invention is preferably less than 60 µg/ml e.g. ≤55 µg/ml, ≤50 µg/ml, ≤45 µg/ml, ≤40 µg/ml, etc. A concentration of about 20 µg/ml is typical.

The concentration of diphtheria toxoid in a composition of invention is typically at least 50 IU/ml.

The concentration of tetanus toxoid in a composition of the invention is typically at least 100 IU/ml.

The ratio of diphtheria toxoid to tetanus toxoid in compositions of the invention is usually between 2:1 and 3:1 (measured in Lf units), preferably between 2.4:1 and 2.6:1, and is more preferably 2.5:1.

The amount of wP antigen in compositions of the invention is typically at least 8 IU/ml.

The amount of Hib conjugate, measured as saccharide, in compositions of the invention is typically between 10 and 30 µg/ml.

The amount of HAV antigen, measured in EU (Elisa Units), is typically at least 600 EU/ml.

The amount of IPV antigen depends on the strain serotype. For a type 1 virus, a composition typically contains about 80 DU/ml. For a type 2 virus, a composition typically contains about 16 DU/ml. For a type 3 virus, a composition typically contains about 65 DU/ml.

The amount of a meningococcal conjugate, measured as saccharide, in compositions of the invention is typically between 5 and 25 µl/ml for each serogroup.

The amount of a pneumococcal conjugate, measured as saccharide, in compositions of the invention is typically between 2 and 20 µg/ml for each serotype.

Compositions of the invention are preferably administered to patients in 0.5 ml doses. References to 0.5 ml doses will be understood to include normal variance e.g. 0.5 ml±0.05 ml.

The invention can provide bulk material which is suitable for packaging into individual doses, which can then be distributed for administration to patients. Concentrations mentioned above are, typically concentrations in final packaged dose, and so concentrations in bulk vaccine may be higher (e.g. to be reduced to final concentrations by dilution).

Compositions of the invention will generally be in aqueous form.

Residual material from individual antigenic components may also be present in trace amounts in the final vaccine produced by the process of the invention. For example, if formaldehyde is used to prepare the toxoids of diphtheria, tetanus and pertussis then the final vaccine product may retain trace amounts of formaldehyde (e.g. less than 10 µg/ml, preferably <5 µg/ml). Media or stabilizers may have been used during poliovirus preparation (e.g. Medium 199), and these may carry through to the final vaccine. Similarly, free amino acids (e.g. alanine, arginine, aspartate, cysteine and/or cystine, glutamate, glutamine, glycine, histidine, proline and/or hydroxyproline, isoleucine, leucine, lysine, methionine, phenylalanine, serine, threonine, tryptophan, tyrosine and/or valine), vitamins (e.g. choline, ascorbate, etc.), disodium phosphate, monopotassium phosphate, calcium, glucose, adenine sulfate, phenol red, sodium acetate, potassium chloride, etc. may be retained in the final vaccine at ≤100 µg/ml, preferably <10 µg/ml, each. Other components from antigen preparations, such as neomycin (e.g. neomycin sulfate, particularly from the IPV component), polymyxin B (e.g. polymyxin B sulfate, particularly from the IPV component), etc. may also be present at sub-nanogram amounts per dose. A further possible component of the final vaccine which originates in the antigen preparations arises from less-than-total purification of antigens. Small amounts of *B. pertussis, C. diphtheriae, C. tetani* and *S. cerevisiae* proteins and/or genomic DNA may therefore be present. To minimize the amounts of these residual components, antigen preparations are preferably treated to remove them prior to the antigens being used in the process of the invention.

Where an IPV component is used, it will generally have been grown on Vero cells. The final vaccine preferably contains less than 10 ng/ml, preferably ≤1 ng/ml e.g. ≤500 pg/ml or ≤50 pg/ml of Vero cell DNA e.g. less than 10 ng/ml of Vero cell DNA that is ≥50 base pairs long.

Packaging Compositions of the Invention

After combining the HBsAg and the adjuvants, the processes of the invention may comprise a step of extracting and packaging a 0.5 ml sample of the mixture into a container. For multidose situations, multiple dose amounts will be extracted and packaged together in a single container. The processes of the invention may comprise the further step of packaging the vaccine into containers for use. Suitable containers include vials and disposable syringes (preferably sterile ones).

Where a composition of the invention is packaged into vials, these are preferably made of a glass or plastic material. The vial is preferably sterilized before the composition is added to it. To avoid problems with latex-sensitive patients, vials are preferably sealed with a latex-free stopper. The vial may include a single dose of vaccine, or it may include more than one dose (a 'multidose' vial) e.g. 10 doses. When using a multidose vial, each dose should be withdrawn with a sterile needle and syringe under strict aseptic conditions, taking care to avoid contaminating the vial contents. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed.

Where the composition is packaged into a syringe, the syringe will not normally have a needle attached to it, although a separate needle may be supplied with the syringe for assembly and use. Safety needles are preferred. 1-inch 23-gauge, 1-inch 25-gauge and ⅝-inch 25-gauge needles are typical. Syringes may be provided with peel-off labels on which the lot number and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of butyl rubber. If the syringe and needle are packaged separately then the needle is preferably fitted with a butyl rubber shield. Grey butyl rubber is preferred. Preferred syringes are those marketed under the trade name "Tip-Lok"™.

Where a glass container (e.g. a syringe or a vial) is used, then it is preferred to use a container made from a borosilicate glass rather than from a soda lime glass.

After a composition is packaged into a container, the container can then be enclosed within a box for distribution e.g. inside a cardboard box, and the box will be labeled with details of the vaccine e.g. its trade name, a list of the antigens in the vaccine (e.g. 'hepatitis B recombinant', etc.), the presentation container (e.g. 'Disposable Prefilled Tip-Lok Syringes' or '10×0.5 ml Single-Dose Vials'), its dose (e.g. 'each containing one 0.5 ml dose'), warnings (e.g. 'For Adult Use Only' or 'For Pediatric Use Only'), an expiration date, an indication (e.g. 'active immunisation against hepatitis B virus (HBV) infection caused by all known subtypes for patients with renal insufficiency (including pre-haemodialysis and haemodialysis) patients, from the age of 15 years onwards', etc.), a patent number, etc. Each box might contain more than one packaged vaccine e.g. five or ten packaged vaccines (particularly for vials). If the vaccine is contained in a syringe then the package may show a picture of the syringe.

The vaccine may be packaged together (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

The packaged vaccine is preferably stored at between 2° C. and 8° C. It should not be frozen. Vaccines can be provided in full-liquid form (i.e. where all antigenic components are in aqueous solution or suspension) during manufacture, or they can be prepared in a form where some components are in liquid form and others are in a lyophilized form. Thus a final vaccine can be prepared extemporaneously at the time of use by mixing together two components: (a) a first component comprising aqueous antigens; and (b) a second component comprising lyophilized antigens. The two components are preferably in separate containers (e.g. vials and/or syringes), and the invention provides a kit comprising components (a) and (b). This format is particularly useful for vaccines that include a conjugate component, particularly Hib and/or meningococcal and/or pneumococcal conjugates, as these may be more stable in lyophilized form. Thus conjugates may be lyophilised prior to their use with the invention. Further components may also be added prior to freeze-drying e.g. as stabilizers. Preferred stabilizers for inclusion are lactose, sucrose and mannitol, as well as mixtures thereof e.g. lactose/sucrose mixtures, sucrose/mannitol mixtures, etc. The final vaccine may thus contain lactose and/or sucrose. Using a sucrose/mannitol mixture can speed up the drying process.

Thus the invention provides a process for preparing a two-container combination vaccine, comprising the following steps:

preparing an aqueous combination vaccine as described above, but wherein the said one or more antigens does not include a conjugated capsular saccharide antigen;

packaging said combination vaccine in a first container (e.g. a syringe);

preparing a conjugated capsular saccharide antigen in lyophilised form;

packaging said lyophilised antigen in a second container (e.g. a vial); and packaging the first container and second container together in a kit.

The kit can then be distributed to physicians.

D, T, P and HBsAg components are preferably in liquid form.

Methods of Treatment and Administration of the Vaccine

Compositions of the invention are suitable for administration to human patients, and the invention provides a method of raising an immune response in a patient, comprising the step of administering a composition of the invention to the patient.

The invention also provides a composition of the invention for use in medicine.

The invention also provides the use of (i) HBsAg purified from recombinant yeast cells, wherein the purification process involves disrupting the yeast cells in the presence of a non-ionic surfactant, and (ii) one or more non-HBV antigens, in the manufacture of a medicament for administering to a patient.

Immunogenic compositions of the invention are preferably vaccines, for use in the prevention and/or treatment of at least hepatitis B virus infection. Patients who have received compositions of the invention preferably have a serum anti-HBsAg GM titer of ≥500 mIU/ml, measured 6 weeks after the first immunisation. More preferably, the titer is ≥500 mIU/ml, when measured after 12 months.

In order to have full efficacy, a typical primary immunization schedule for a child may involve administering more than one dose. For example, doses may be at: 0 & 6 months (time 0 being the first dose); at 0, 1, 2 & 6 months; at day 0, day 21 and then a third dose between 6 & 12 months; at 2, 4 & 6 months; at 3, 4 & 5 months; at 6, 10 & 14 weeks; or at 0, 1, 2, 6 & 12 months.

Compositions can also be used as booster doses e.g. for children, in the second year of life.

Compositions of the invention can be administered by intramuscular injection e.g. into the arm or leg Vaccines produced by the invention may be administered to patients at the same time as a separate pneumococcal conjugate vaccine, such as Prevnar™.

Where compositions of the invention include an aluminium-based adjuvant, settling of components may occur during storage. The composition should therefore be shaken prior to administration to a patient. The shaken composition will be a turbid white suspension.

Preferred Vaccines

Specific multivalent immunogenic compositions of the invention include:

- A pentavalent composition comprising HBsAg, D, T, Pa and IPV. The vaccine is in aqueous form. It includes both aluminium hydroxide and aluminium phosphate adjuvants. HBsAg is adsorbed to aluminium phosphate. D, T and Pa are adsorbed to aluminium hydroxide. Amounts per ml: about 50 Lf diphtheria toxoid; about 20 Lf tetanus toxoid; about 50 μg PT; about 50 μg FHA; about 16 μg pertactin; about 20 μg HBsAg; about 80 DU type 1 poliovirus; about 16 DU type 2 poliovirus; about 64 DU type 3 poliovirus. Dose: about 0.5 ml. May be presented in pre-filled syringe.
- A pentavalent composition comprising HBsAg, D, T, Pa and IPV. The vaccine is in aqueous form. It includes both aluminium hydroxide and aluminium phosphate adjuvants. HBsAg is adsorbed to aluminium phosphate. D, T and Pa are adsorbed to aluminium hydroxide. Amounts per ml: at least 60 IU diphtheria toxoid; at least 80 IU tetanus toxoid; about 50 μg PT; about 50 μg FHA; about 16 μg pertactin; about 20 μg HBsAg; about 80 DU type 1 poliovirus; about 16 DU type 2 poliovirus; about 64 DU type 3 poliovirus. Dose: about 0.5 ml. May be presented in pre-filled syringe.
- A tetravalent composition comprising HBsAg, D, T and Pw. The components are in aqueous form. It includes both aluminium hydroxide and aluminium phosphate adjuvants. HBsAg is adsorbed to aluminium phosphate. D and T are adsorbed to aluminium hydroxide. The composition includes thimerosal, but preferably does not contain 2-phenoxyethanol. Amounts per ml: at least 60 IU diphtheria toxoid; at least 120 IU tetanus toxoid; at least 8 IU Pw; about 20 μg HBsAg. Dose: about 0.5 ml.
- A pentavalent composition comprising HBsAg, D, T, Pw and a Hib-T conjugate. The HBsAg, D, T and Pw components are in aqueous form; the Hib-T is lyophilised. It includes both aluminium hydroxide and aluminium phosphate adjuvants. D and T are adsorbed to aluminium hydroxide. HBsAg and Hib-T are adsorbed to aluminium phosphate. The lyophilized Hib-T includes lactose. The aqueous component may include thimerosal. Amounts per ml: at least 60 IU diphtheria toxoid; at least 120 IU tetanus toxoid (plus between 5-25 μg tetanus toxoid as carrier in Hib-T); at least 8 IU Pw; about 20 μg HBsAg; about 5 μg Hib-T, measured as saccharide. Dose: about 0.5 ml.
- A heptavalent composition comprising HBsAg, D, T, Pw and three conjugates: a Hib-T conjugate, a MenA conjugate and a MenC conjugate. The HBsAg, D, T and Pw components are in aqueous form; the three conjugates are lyophilised. It includes both aluminium hydroxide and aluminium phosphate adjuvants. D and T are adsorbed to aluminium hydroxide. HBsAg is adsorbed to aluminium phosphate. The lyophilized component may include lactose and/or sucrose. The aqueous component may include thimerosal. Potential amounts per ml: at least 60 IU diphtheria toxoid; at least 120 IU tetanus toxoid (plus between 5-25 μg tetanus toxoid as carrier in Hib-T); at least 8 IU Pw; about 20 μg HBsAg; about 5 μg of each conjugate, measured as saccharide. Dose: about 0.5 ml.

These compositions can be used as vaccines on their own, or as components of further vaccines. For example, the invention provides a hexavalent composition comprising the pentavalent HBsAg-D-T-Pa-IPV composition described above, plus a lyophilized Hib-T conjugate. The lyophilized Hib-T is preferably not adsorbed to an aluminium salt. The invention also provides a heptavalent composition comprising the pentavalent HBsAg-D-T-Pa-IPV composition described above, plus lyophilized Hib-T and MenC conjugates. The invention also provides an octavalent composition comprising the pentavalent HBsAg-D-T-Pa-IPV composition described above, plus lyophilized Hib-T, MenC and MenY conjugates. The invention also provides a pentavalent composition comprising the tetravalent HBsAg-D-T-Pw composition described above, plus a lyophilized Hib-T conjugate. The invention also provides a heptavalent composition comprising the tetravalent HBsAg-D-T-Pw composition described above, plus a lyophilized mixture of Hib-T conjugate, MenA conjugate and MenC conjugate. The final vaccines can be prepared by reconstituting the lyophilized materials with the aqueous HBsAg-containing materials at the time of use, and the lyophilized and aqueous components are preferably packaged together in a kit, as described above.

Specific processes of the invention include those comprising the following steps:

- Purify HBsAg according to invention; adsorb HBsAg to aluminium phosphate adjuvant; obtain thimerosal-free bivalent D-T mixture with aluminium hydroxide adjuvant; obtain PT, FHA and pertactin for Pa component; obtain IPV antigens, as pooled types 1, 2 and 3, preferably without aluminium salt adjuvant; combine D-T, Pa, IPV and HBsAg, in any order, to give final pentavalent combination; optionally, package into syringe.
- Purify HBsAg according to invention; adsorb HBsAg to aluminium phosphate adjuvant; obtain 2-phenoxyethanol-free, thimerosal-containing trivalent D-T-Pw mixture with aluminium hydroxide and aluminium phosphate adjuvants; combine D-T-Pw and HBsAg to give final tetravalent combination; optionally, package into syringe; optionally, package in combination with lyophilized conjugate component(s) e.g. Hib-T, MenA, MenC.
- Purify HBsAg according to invention; adsorb HBsAg to aluminium phosphate adjuvant; obtain 2-phenoxyethanol-free, thimerosal-containing trivalent D-T-Pw mixture with aluminium hydroxide and aluminium phosphate adjuvants; obtain lyophilized Hib-T conjugate; combine D-T-Pw and HBsAg to give aqueous tetravalent component; package aqueous tetravalent component into glass vial; package lyophilized Hib-T and/or MenC and/or MenY into glass vial; combine the two vials to be presented in a single kit for reconstitution to give a pentavalent combination vaccine. The glass vials can be type I glass and have rubber butyl stoppers.
- Purify HBsAg according to invention; adsorb HBsAg to aluminium phosphate adjuvant; obtain 2-phenoxyethanol-free, thimerosal-containing trivalent D-T-Pw mixture with aluminium hydroxide and aluminium phosphate adjuvants; obtain IPV antigens, as pooled types 1, 2 and 3, preferably without aluminium salt adjuvant; combine D-T-Pw, IPV and HBsAg in any order to give final pentavalent combination; optionally, package into syringe; optionally, package in combination with lyophilized conjugate component(s) e.g. Hib-T, MenA, MenC.

Further components may be added at any stage e.g. sodium chloride, adjuvants, preservatives, etc. These processes can be used e.g. to prepare the vaccines described above.

The different process steps may be performed at substantially the same time, or may be performed separately. They can be performed in the same location or in different locations, even in different countries e.g. HBsAg purification may take place in a different place from Hib-T lyophilisation.

Carrier Proteins for Conjugates

Conjugated saccharide antigens include a carrier protein, to which the saccharide is covalently attached, either directly or via a linker. General information on conjugation techniques can be found in reference 45.

Various proteins are known for use as carriers, and preferred carrier proteins are bacterial toxins or toxoids, such as diphtheria toxoid or tetanus toxoid. Other suitable carrier proteins include, but are not limited to, the CRM197 mutant of diphtheria toxin [75-77], the *N. meningitidis* outer membrane protein [78], synthetic peptides [79, 80], heat shock proteins [81,82], pertussis proteins [83,84], cytokines [85], lymphokines [85], hormones [85], growth factors [85], artificial proteins comprising multiple human CD4+ T cell epitopes from various pathogen-derived antigens [86] such as N19 [87], protein D from *H. influenzae* [88,89], pneumococcal surface protein PspA [90], pneumolysin [91], iron-uptake proteins [92], toxin A or B from *C. difficile* [93], *S. agalactiae* proteins [94], etc.

Attachment of a saccharide to a carrier is preferably via a —$NH_2$ group e.g. in the side chain of a lysine residue in a carrier protein, or of an arginine residue. Attachment to —SH groups (e.g. in the side chain of a cysteine) is also possible.

Conjugates with a saccharide:protein ratio (w/w) of between 1:5 (i.e. excess protein) and 5:1 (i.e. excess saccharide) are preferred.

Compositions may include a small amount of free carrier. Ignoring any carrier included as a separate antigen, unconjugated carrier is preferably no more than 5% of the total amount of the carrier protein in the composition as a whole, and more preferably present at less than 2% by weight.

It is possible to include more than one type of carrier protein in a composition e.g. to reduce the risk of carrier suppression.

The carrier protein used for *N. meningitidis* conjugates may be protein D from *H. influenzae*. This protein is described in detail in references 95 & 96, and its use as a carrier protein in conjugates is described in reference 97. The term "protein D" includes fragments of the native full-length protein, as disclosed in reference 97, and also fusion proteins comprising either full-length protein D or these fragments (e.g. a fusion of a fragment of influenza virus NS1 protein and a fragment of protein D). The fragments will retain the ability to convert a T-independent saccharide antigens into a T-dependent antigen when conjugated thereto. Typical fragments will include at least the N-terminal ⅓ of protein D. The protein can conveniently be expressed in *E. coli* [96], and this recombinant material is preferred for use with the invention [97].

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where an antigen is described as being "adsorbed" to an adjuvant, it is preferred that at least 50% (by weight) of that antigen is adsorbed e.g. 50%, 60%, 70%, 80%, 90%, 95%, 98% or more. It is preferred that diphtheria toxoid and tetanus toxoid are both totally adsorbed i.e. none is detectable in supernatant. Total adsorption of HBsAg can be used.

Quantities of diphtheria toxoid can be expressed in international units (IU). For example, the NIBSC supplies the 'Diphtheria Toxoid Adsorbed Third International Standard 1999' [98,99], which contains 160 IU per ampoule. As an alternative to the IU system, the 'Lf' unit ("flocculating units" or the "limes flocculating dose") is defined as the amount of toxoid which, when mixed with one International Unit of antitoxin, produces an optimally flocculating mixture [100]. For example, the NIBSC supplies 'Diphtheria Toxoid, Plain' [101], which contains 300 LF per ampoule, and also supplies 'The 1st International Reference Reagent For Diphtheria Toxoid For Flocculation Test' [102] which contains 900 LF per ampoule.

Quantities of tetanus toxoid can be expressed in international units (IU). For example, the NIBSC supplies the 'Tetanus Toxoid Adsorbed Third International Standard 2000' [103,104], which contains 469 IU per ampoule. As an alternative to the IU system, the 'Lf' unit ("flocculating units" or the "limes flocculating dose") is defined as the amount of toxoid which, when mixed with one International Unit of antitoxin, produces an optimally flocculating mixture [100]. For example, the NIBSC supplies 'The 1st International Reference Reagent for Tetanus Toxoid For Flocculation Test' [105] which contains 1000 LF per ampoule.

Quantities of wP antigens can be expressed in international units (IU). For example, the NIBSC supplies the 'Third International Standard For Pertussis Vaccine' [106], which contains 46 IU per ampoule. Each ampoule contains the freeze-dried residue of 2.0 ml aliquots of an aqueous solution which contained 10 liters of bacterial suspension (equivalent to 180 opacity units in terms of the U.S. Opacity Standard) diluted with eight liters of M/15 Sorensen's buffer pH 7.0. As an alternative to the IU system, the 'OU' unit ("opacity units") is also used (e.g. 40 U may be about 1 IU).

Amounts of conjugates are generally given in terms of mass of saccharide (i.e. the dose of the conjugate (carrier+saccharide) as a whole is higher than the stated dose) in order to avoid variation due to choice of carrier.

Where animal (and particularly bovine) materials are used in the culture of cells, they should be obtained from sources that are free from transmissible spongiform encaphalopathies (TSEs), and in particular free from bovine spongiform encephalopathy (BSE).

BRIEF DESCRIPTION OF THE DRAWINGS

FIG. 1 is a copy of FIG. 2 from references 3 and 4, which state that the figure illustrates "antigenicity and immunity based on an adsorption method wherein sample 1 is a sample in which surplus aluminum hydroxide gel is added after a combination of each component vaccine is completed, and sample 2 is a sample in which the said adsorbent of the same concentration is previously added before the combination is completed". FIGS. 1A & 1B illustrate relative antigenicity of samples 1 and 2, respectively.

FIG. 2 shows western blot results for HBsAg stability in a composition. In FIG. 2A, the lanes numbered 1-10 at the top of the figure are (1) Laemmli sample buffer (LSB); (2) MW markers; (3-5) 1 µg of three separate control HBsAg preparations; (6-8) supernatant of three separate pentavalent lots; (9-10) LSB. In FIGS. 2B & 2C, the lanes numbered 1-10 at the top of the figure are: (1) MW markers, (2-4) 1 µg of three separate control HBsAg preparations; (5-7) supernatant of three separate pentavalent lots, stored for 2 weeks at 2-8° C.; (8-10) supernatant of three separate pentavalent lots, stored for 2 weeks at 36-38° C.

FIG. 3 shows the variation of pH over time for a pentavalent composition.

FIG. 4 shows western blot results for HBsAg stability in an octavalent composition. In FIGS. 4A and 4B, lanes numbered 1-3 at the top of the figure are as follows: lane 1 contains MW markers; lane 2 contains a HBsAg control at 1 µg/ml; lane 3 contains the supernatant of the octavalent composition. In FIG. 4B, lanes numbered 4-6 are as follows: lane 4 contains LSB; lane 5 contains the same control as lane 2; lane 6 contains a DOC/TCA extract.

MODES FOR CARRYING OUT THE INVENTION

HBsAg Expression and Purification

Figure 1C:
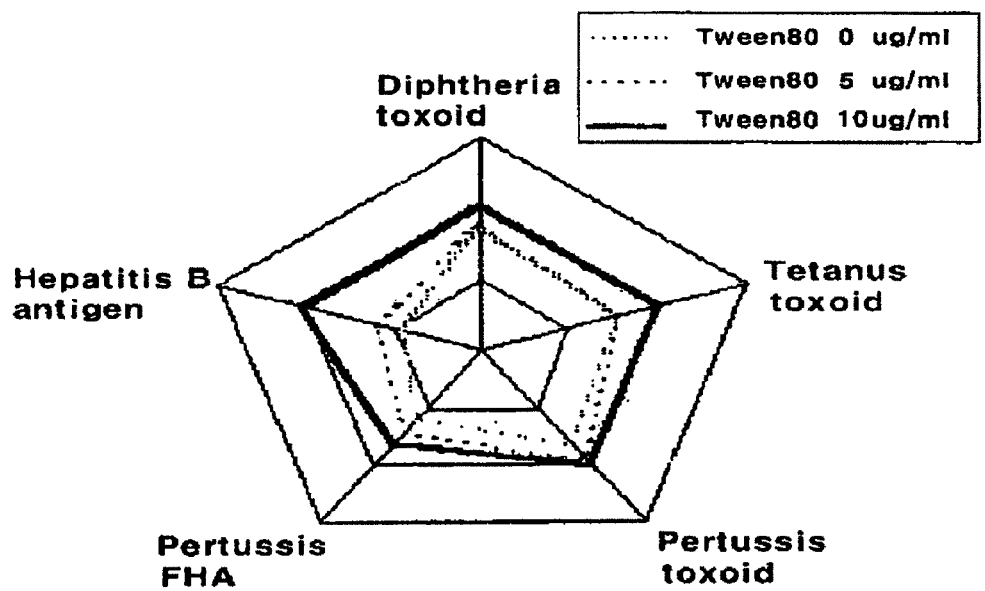
FIGS. 1C & 1D illustrate the relative level of antibody formation against each antigen of samples 1 and 2, respectively.
Figure 1D:
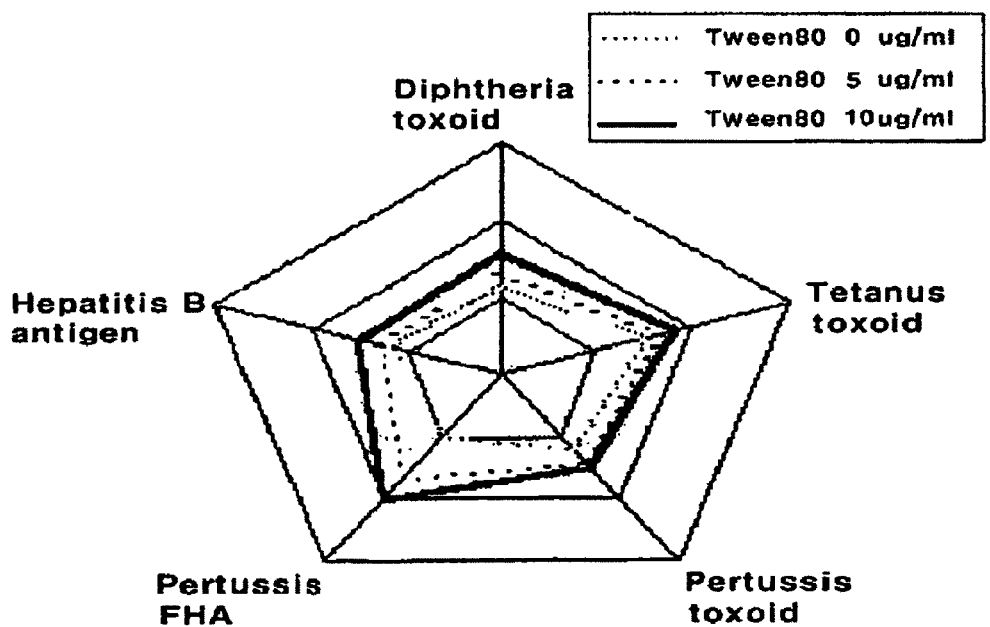

A *H. polymorpha* yeast host encoding HBsAg [107,108] was prepared. 100 liters of medium was prepared in a 300 liter fermenter and inoculated with the yeast. Fermentation was continued until the cells were present at 100 grams/liter. At this stage, as the host is methyloptrophic, methanol was added, and fermentation was stopped. The volume of the final culture was 160-170 liters. Cells were harvested from the culture medium by centrifugation.

Rather than adding non-ionic surfactants to the HBsAg after purification, as described in references 3 and 4, surfactant was used during purification of the protein. In particular, the harvested yeast cells were suspended in phosphate buffer containing 0.1-0.2% polysorbate 20 and 10 mM EDTA. The suspension was cooled and disrupted using a high pressure liquid homogenizer.

The homogenized cell suspension was then clarified by centrifugation. After addition of NaCl to the supernatant, polyethylene glycol was added slowly to a concentration of 3-5% for precipitation. The solution was stirred for 5 minutes, left standing for 30 minutes and centrifuged for 10 minutes. Further PEG was added slowly to the supernatant to 8-10%, stirred and left standing for 2 hours. This solution was centrifuged for 10 minutes.

Fumed silica was added to the supernatant at a concentration of 1-2%. The solution was stirred for 12 hours, centrifuged, and the precipitate was dissolved completely in borax buffer containing sodium deoxycholate. After shaking for 100-120 minutes in a water bath the solution was centrifuged and the supernatant was collected. The supernatant was loaded onto a DEAE column which had been equilibrated with Tris/Cl buffer at a flow rate 200 mL/min, and eluted with Tris/Cl buffer, containing NaCl solution. Cesium chloride was added to the DEAE eluate up to a concentration of 1.2 g/mL and the solution was ultracentrifuged at 40,000 rpm. The desalted CsCl pool was diluted with PBS to a protein concentration of 400 µg/ml, formalin was added to a concentration of 0.025%, and the mixture was left standing for 72 hours. Finally, residual formalin was removed using PBS.

Thus HBsAg was purified with inclusion of polysorbate 20, but the surfactant was added prior to disruption of the recombinant cells, rather than being added after the antigen was purified.

Full Liquid Multivalent Vaccines

Yeast-expressed HBsAg, diphtheria toxoid, tetanus toxoid and whole-cell pertussis antigens were added to a suspension of an aluminium salt adjuvant. The pH of the mixture was adjusted, and then a Hib-CRM197 conjugate was added, such that it did not become adsorbed to the aluminium adjuvant. This process gave a pentavalent vaccine with the following composition:

| Component | Concentration |
|---|---|
| Diphtheria toxoid | 15 Lf/ml |
| Tetanus toxoid | 6.5 Lf/ml |
| Whole cell pertussis antigen | 30 OU/ml |
| HBsAg | 20 µg/ml |
| CRM-Hib | 20 µg/ml |
|  | (as saccharide) |
| $Al^{3+}$ | 0.6 mg/ml |
| NaCl | 9 mg/ml |

In further work, separate meningococcal-CRM197 conjugates from each of serogroups C, W135 and Y were added after the CRM-Hib component in order to give an octavalent vaccine:

| Component | Concentration |
|---|---|
| Diphtheria toxoid | 15 Lf/ml |
| Tetanus toxoid | 6.5 Lf/ml |
| Whole cell pertussis antigen | 30 OU/ml |
| HBsAg | 20 µg/ml |
| CRM-Hib | 20 µg/ml |
| CRM-MenC | 20 µg/ml |
| CRM-MenW135 | 20 µg/ml |
| CRM-MenY | 20 µg/ml |
| $Al^{3+}$ | 0.6 mg/ml |
| NaCl | 9 mg/ml |

An important parameter for vaccine stability and efficacy is the percentage of hydrolysis of Hib conjugate, the clinical limit being 25% free saccharide (reference 109 reports that 20% did not affect clinical immunogenicity). This parameter was measured in the pentavalent vaccine by HPAEC-PAD, which permits direct quantification of non-conjugated carbohydrates at picomolar levels with minimal separation and clean-up. Analysis focused on the amount of free saccharide.

The amount of free saccharide was assayed and expressed as a percentage of the total amount. Results were as follows:

| Lot | Time | Free |
|---|---|---|
| 1 | 0 | 5.3% |
|  | 2 weeks, 2-8° C. | 5.7% |
|  | 2 weeks, 36-38° C. | 6.8% |
|  | 4 weeks, 2-8° C. | 6.5% |
|  | 4 weeks, 36-38° C. | 11.6% |
| 2 | 0 | 3.0% |
|  | 2 weeks, 2-8° C. | 3.1% |
|  | 2 weeks, 36-38° C. | 5.5% |
|  | 4 weeks, 2-8° C. | 3.7% |
|  | 4 weeks, 36-38° C. | 8.1% |

-continued

| Lot | Time | Free |
| --- | --- | --- |
| 3 | 0 | 3.3% |
| | 2 weeks, 2-8° C. | 4.0% |
| | 2 weeks, 36-38° C. | 6.3% |
| | 4 weeks, 2-8° C. | 4.1% |
| | 4 weeks, 36-38° C. | 8.7% |

A maximum of 25% free saccharide is clinically acceptable. All values were below this threshold, and were below 6.5% for up to 4 weeks at 2-8° C. Under thermal stress conditions (4 weeks at 36-38° C.) a higher level was seen, but stil well below the 25% value, with the maximum being 11.6% for lot 1. Earlier work on multivalent Hib vaccines has shown that one month of storage at 36-38° C. gives more CRM-Hib hydrolysis than two years of storage at 2-8° C. Acceptable hydrolysis can thus be expected over at least a 2 year time-scale under normal storage conditions.

HPAEC-PAD analysis of free saccharide was also carried out after 6 months at 2-8° C. The data were as follows:

| Lot | Free |
| --- | --- |
| 1 | 8.3% |
| 2 | 5.5% |
| 3 | 5.8% |

Thus there is only a small increase in the percentage of free saccharide at 6 months compared to 4 weeks, with values still well below the 25% value. CRM197-Hib is thus very stable in the three formulations.

FIG. 3A shows variation of pH in the pentavalent vaccine over 6 months for three lots stored at 2-8° C. FIG. 3B shows variation of pH over 4 weeks for three lots stored at 36-38° C. At 2-8° C. pH was stable over 6 months, while under thermal stress conditions there was a slight drop of 0.1 pH unit after 2 weeks and a further slight drop after 4 weeks. Even so, all pH values remained within the accepted range of 6.0-7.0.

Osmolarity of all three pentavalent lots was between 312 and 315 mOsm/Kg, centrally within the target range of 240-360 mOsm/Kg for injectable vaccines.

Evaluation of the potency and immunogenicity of antigens is important in order to assess the efficacy of a combination vaccine. The potency of Diphtheria, Tetanus and Pertussis antigens in the pentavalent vaccine was evaluated and the immunogenicity of both CRM-Hib and HBsAg was tested. ELISA analysis was carried out to evaluate the level of specific antibodies after immunisation. Immunogenicity of HBsAg was performed using a mouse model and a different immunisation schedule with respect to that used for the HBV potency.

DTP potency values were as follows:

| | D | T | P |
| --- | --- | --- | --- |
| Lot 1 | 41 | 161 | 4 |
| Lot 2 | 39 | 138 | 5 |
| Lot 3 | 39 | 143 | 6 |

For each of these three antigens the potency test results are all significantly above accepted lower limits and these results indicate good efficacy for these three antigens.

For assessing HBsAg immunogenicity, groups of 10 CD1 mice received the pentavalent vaccine by subcutaneous injection (0.5 ml, diluted 1:4 in saline) at days 0 and 14. The mice were bled on day 21 and HBsAg-specific antibodies were assessed by ELISA using either (a) the "Enzygnost Anti-HBs II" test (Dade Behring) or (b) the "Ausab EIA" test (Abbott). These ELISA tests have different formats and different sensitivities to HBsAg. Geometric Mean Titre values are thus not comparable between the two tests. However, within the scope of each test the GMT values for the sera were optimal. Results were as follows:

| | Enzygnost | | Ausab EIA | |
| --- | --- | --- | --- | --- |
| | GMT | % responders | GMT | % responders |
| Lot 1 | 1008 | 100 | 192 | 100 |
| Lot 2 | 1518 | 100 | 194 | 100 |
| Lot 3 | 461 | 90 | 127 | 100 |
| Adjuvant only | 2 | 0 | 2 | 0 |

All the GMT values obtained performing this kind of mouse immunogenicity assay are higher than the values reported in the literature. The percentage of responders is consistently high for both antigens at an optimum level of ~100%.

For assessing Hib immunogenicity, groups of 8 CD1 mice received the pentavalent vaccine by subcutaneous injection (0.5 ml, diluted 1:4 in saline) at days 0, 10 and 20. The mice were bled on day 34 and Hib-specific antibodies were assessed by ELISA. Results were as follows:

| | % responders |
| --- | --- |
| Lot 1 | 100 |
| Lot 2 | 100 |
| Lot 3 | 100 |
| Adjuvant only | 0 |

Adsorption of HBsAg to the aluminium adjuvant is an important factor for vaccine immunogenicity, and this parameter was measured by immunoblot. The immunoblot procedure followed was essentially as follows: a 1 ml volume of vaccine supernatant was DOC/TCA precipitated and denatured with LSB and then loaded on a 12% acrylamide SDS-PAGE; 1 µg of each lot of HBsAg was loaded as control; a goat anti-HBsAg antibody preparation was used as primary antibody (diluted 1:1000) and an anti-goat POD conjugate (diluted 1:2500) was used as secondary antibody.

Figure 2C:
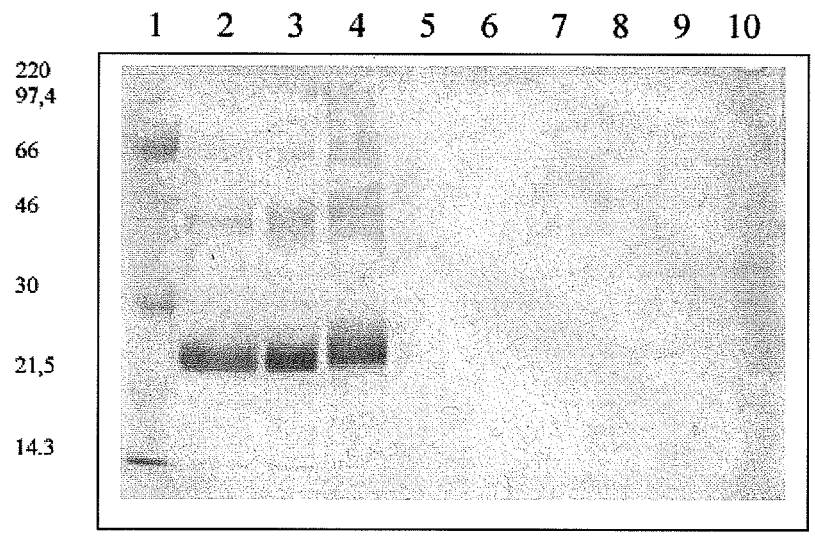

Results for the pentavalent vaccine are shown in FIG. 2. Lanes 6-8 of FIG. 2A show that there is no detectable soluble HBsAg in the composition at time zero, and lanes 5-10 of FIGS. 2B & 2C confirm that this remains true after 2 weeks and 4 weeks of storage at 2-8° C. or 36-38° C. In three different lots, ~99% of HBsAg remains adsorbed onto the adjuvant under these various conditions.

Figure 2D:
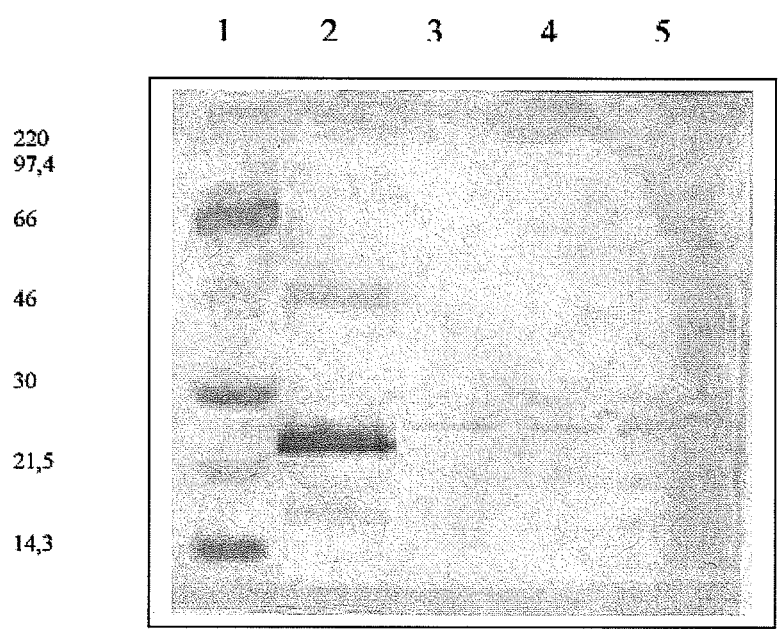
In FIG. 2D, the lanes numbered 1-5 at the top of the figure are: (1) MW markers; (2) control HBsAg; (3-5) supernatant of three separate pentavalent lots. Numbers to the left side of FIGS. 2A-2D represent molecular weights.

An additional stability assay was performed after 6 months of storage at 2-8° C. (FIG. 2D). Adsorption remained at ~99% for each of the three lots.

The positive controls used in FIG. 2 contained 1 µg HBsAg. A single band corresponding to the S peptide (24 kDa) was seen, plus a band characteristic of aggregates (~45 kDa). Pre-S2 was not seen.

The octavalent vaccine was also tested for HBsAg adsorption in a similar way. A 1 ml sample was centrifuged at 3500 rpm for 10 minutes. The supernatant was removed to a fresh tube and precipitated with DOC/TCA. The pellet was resuspended in 200 µl extraction buffer, boiled for 5 minutes and centrifuged at 1300 rpm for 10 minutes. 20 µl of this extract and the supernatant precipitated with DOC/TCA were loaded on 12% SDS-PAGE for Western-Blot.

FIG. 4A shows the octavalent vaccine at time zero, and FIG. 4B shows the vaccine after 8 months of storage at 2-8° C. The absence of any significant staining in lanes 3 & 6 of FIG. 4B (certainly less staining than seen with 1 μg of HBsAg in control lanes 2 & 5) shows that HBsAg adsorption remains stable over this storage period.

Liquid/Lyophilised Multivalent Vaccine

Three antigenic components are collected as follows:

A TRIVALENT D-T-Pw COMPONENT: A D-T-Pw component was prepared that includes diphtheria toxoid adsorbed to an aluminium hydroxide adjuvant, tetanus toxoid also adsorbed to an aluminium hydroxide adjuvant, and whole-cell pertussis antigens. The D-T-Pw component also includes an aluminium phosphate adjuvant. This component contains thimerosal, but contains no 2-phenoxyethanol.

A HBsAg COMPONENT: HBsAg is expressed and purified from a recombinant yeast and is adsorbed onto an aluminium phosphate antigen [110].

A Hib CONJUGATE COMPONENT: Hib polysaccharide is prepared from Hib, strain 20752 and after activation with cyanogen bromide and derivatisation with an adipic hydrazide spacer is covalently coupled to a tetanus toxoid via carbodiimide condensation, at a saccharide:carrier weight ratio of about 1:3. The conjugate is adsorbed to an aluminium phosphate adjuvant [64] and then lyophilised with lactose.

The D-T-Pw component is mixed with the HBsAg component. The HBsAg level is 20 μg/ml. The D level is ≥60 IU. The T level is ≥120 IU. The Pw level is ≥8 IU. The tetravalent mixture, in the form of a turbid white suspension, is packaged in aqueous form into glass vials with a rubber butyl stopper, to contain 1 dose (0.5 ml), 2 doses (1 ml) or 10 doses (5 ml). The lyophilised Hib component is also placed into vials. The amount of powder per vial is measured to give 5 μg/ml (measured as saccharide) after reconstitution, with 1 dose, 2 doses or 10 doses per vial.

The two vials are packaged together in boxes. Boxes contain either 1 vial of each component (either single dose or multidose vials) or 100 vials of each component.

For patient administration, the aqueous D-T-Pw-HBsAg material is withdrawn into a syringe, and is introduced into the lyophilised conjugate vial. After the lyophilised material is reactivated, it is withdrawn back into the syringe through a fresh needle, to give a pentavalent vaccine ready for administration to patients. Various 3-dose primary immunisation schedules can be used: 2, 4 & 6 months; 3, 4, & 5 months; or 6, 10 & 14 weeks. The vaccine can also be used as a booster in the second year of life.

The 10 dose vials give enough material for immunising 10 patients from a single vial. Reconstitution uses a first syringe, and then individual doses are extracted with new syringes, one dose per syringe. In an alternative (less preferred) arrangement, the 10 doses are withdrawn into a single syringe, with the needle being changed between patients.

It will be understood that the invention has been described by way of example only and modifications may be made whilst remaining within the scope and spirit of the invention.

REFERENCES (The Contents of which are Hereby Incorporated by Reference)

[1] *Vaccines*. (eds. Plotkin & Orenstein). 4th edition, 2004, ISBN: 0-7216-9688-0.
[2] U.S. Pat. No. 6,616,931.
[3] WO02/055105.
[4] US2004/0048336.
[5] *Nonionic Surfactants: Organic Chemistry*. Nico M. van Os, ed. ISBN: 0 824 79997 6.
[6] Vanlandschoot et al. (2005) *J Gen Virol* 86:323-31.
[7] Hilleman (1993) pages 17-40 of *Hepatitis B vaccines in clinical practice* ISBN 0-8247-8780-3.
[8] Gerin et al. (1969) *J Virol* 4:763.
[9] Gerin et al. (1969) *J Virol* 7:569.
[10] Siebke et al. (1972) *Acta Pathol Microbiol Scan* sect B 80:935.
[11] Pillot et al. (1976) *J Clin Microbiol* 4:205.
[12] Duimel & Krijnen (1972) *Vox Sang* 23:249.
[13] Neurath et al. (1974) *PNAS USA* 71:2663.
[14] Charm & Wong (1975) *Biotechnol Bioeng* 16:593.
[15] U.S. Pat. No. 4,857,317.
[16] U.S. Pat. No. 4,683,294.
[17] Houwen et al. (1975) *J Immunol Methods* 8:185.
[18] Sitrin et al. (1993) pages 83-101 of *Hepatitis B vaccines in clinical practice* ISBN 0-8247-8780-3.
[19] Wampler et al. (1985) *PNAS USA* 82:6830-4.
[20] Chi et al. (1994) *Ann NY Acad Sci* 721:365-73.
[21] Agraz et al. (1994) *J Chromatogr A* 672:25-33.
[22] Mason et al. (1992) *PNAS USA* 89:11745-9.
[23] Deml et al. (1999) *J Virol Methods* 79:205-17.
[24] Ibarra et al. (1999) *J Chromatogr B Biomed Sci Appl* 735:271-7.
[25] WO90/10058.
[26] Japanese patent application JP63239234.
[27] U.S. Pat. No. 4,694,074.
[28] EP-0341733.
[29] U.S. Pat. No. 5,242,812.
[30] WO02/12287.
[31] Russian patent application RU-2128707.
[32] Hardy et al. (2000) *J Biotechnol* 77:157-67.
[33] Dogan et al. (2000) *Biotechnol Prog* 16:435-41.
[34] WO03/066094.
[35] Rappuoli et al. (1991) *TIBTECH* 9:232-238.
[36] Ramsay et al. (2001) *Lancet* 357(9251):195-196.
[37] Lindberg (1999) *Vaccine* 17 Suppl 2:S28-36.
[38] Buttery & Moxon (2000) *J R Coll Physicians Lond* 34:163-168.
[39] Ahmad & Chapnick (1999) *Infect Dis Clin North Am* 13:113-133, vii.
[40] Goldblatt (1998) *J Med. Microbiol.* 47:563-567.
[41] European patent 0477508.
[42] U.S. Pat. No. 5,306,492.
[43] WO98/427212
[44] *Conjugate Vaccines* (eds. Cruse et al.) ISBN 3805549326, particularly vol. 10:48-114.
[45] Hermanson (1996) *Bioconjugate Techniques ISBN:* 0123423368 or 012342335X.
[46] WO96/40242.
[47] *W. H. O. Tech. Rep. Ser.* 594:51, 1976.
[48] Zielen et al. (2000) *Infect. Immun.* 68:1435-1440.
[49] Darkes & Plosker (2002) *Paediatr Drugs* 4:609-630.
[50] Watson (2000) *Pediatr Infect Dis J* 19:331-332.
[51] Rubin (2000) *Pediatr Clin North Am* 47:269-285, v.
[52] Jedrzejas (2001) *Microbiol Mol Biol Rev* 65:187-207.
[53] Tettelin et al. (2001) *Science* 293:498-506.
[54] Hoskins et al (2001) *J Bacteriol* 183:5709-5717.
[55] Rappuoli (2000) *Curr Opin Microbiol* 3:445-450
[56] Rappuoli (2001) *Vaccine* 19:2688-2691.
[57] Masignani et al. (2002) *Expert Opin Biol Ther* 2:895-905.
[58] Mora et al. (2003) *Drug Discov Today* 8:459-464.

[59] Wizemann et al. (2001) *Infect Immun* 69:1593-1598.
[60] Rigden et al. (2003) *Crit. Rev Biochem Mol Biol* 38:143-168.
[61] WO02/22167.
[62] McMichael & Green (2003) *Curr Opin Investig Drugs* 4:953-8.
[63] Module 6 of WHO's *The immunological basis for immunization series* (Robertson)
[64] WO97/00697.
[65] WO02/00249.
[66] U.S. Pat. No. 6,013,264.
[67] U.S. Pat. No. 4,624,918.
[68] *Vaccine Design: The Subunit and Adjuvant Approach* (eds. Powell & Newman) Plenum Press 1995 (ISBN 0-306-44867-X).
[69] WO90/14837.
[70] U.S. Pat. No. 6,146,632.
[71] WO99/11241.
[72] WO99/12565.
[73] WO98/56414.
[74] Nony et al. (2001) *Vaccine* 27:3645-51.
[75] Anonymous (January 2002) *Research Disclosure*, 453077.
[76] Anderson (1983) *Infect Immun* 39(1):233-238.
[77] Anderson et al. (1985) *J Clin Invest* 76(1):52-59.
[78] EP-A-0372501.
[79] EP-A-0378881.
[80] EP-A-0427347.
[81] WO93/17712
[82] WO94/03208.
[83] WO98/58668.
[84] EP-A-0471177.
[85] WO91/01146
[86] Falugi et al. (2001) *Eur J Immunol* 31:3816-24.
[87] Baraldo et al. (2004) *Infect Immun* 72:4884-87.
[88] EP-A-0594610.
[89] WO00/56360.
[90] WO02/091998.
[91] Kuo et al. (1995) *Infect Immun* 63:2706-13.
[92] WO01/72337
[93] WO00/61761.
[94] WO2004/041157.
[95] WO91/18926 and U.S. Pat. Nos. 5,858,677, 5,888,517, 5,989,828, 6,025,484 & 6,139,846
[96] Janson et al. (1991) *Infect Immun* 59:119-25.
[97] WO00/56360.
[98] Sesardic et al. (2001) *Biologicals* 29:107-22.
[99] NIBSC code: 98/560.
[100] Module 1 of WHO's *The immunological basis for immunization series* (Galazka).
[101] NIBSC code: 69/017.
[102] NIBSC code: DIFT.
[103] Sesardic et al. (2002) *Biologicals* 30:49-68.
[104] NIBSC code: 98/552.
[105] NIBSC code: TEFT.
[106] NIBSC code: 66/303.
[107] Diminsky et al. (1997) *Vaccine* 15:637-47.
[108] Heijtink et al. (2002) *Vaccine* 20:2191-6.
[109] Sturgess et al. (1999) *Vaccine* 17:1169-1178.
[110] WO93/24148.

The invention claimed is:

1. A process for preparing a combination vaccine, wherein the vaccine comprises: (i) a non-ionic surfactant, (ii) a hepatitis B virus (HBV) surface antigen (HBsAg), and (iii) an antigen from at least one non-HBV pathogen, and wherein the process comprises: (a) purifying the HBV surface antigen from recombinant yeast cells, wherein the purification includes a step in which the yeast cells are disrupted in the presence of the non-ionic surfactant, to give a purified HBsAg component wherein the process does not involve a step of adding the non-ionic surfactant as a separate component after HBsAg purification; (b) adsorbing the purified HBsAg component to aluminium phosphate; and (c) combining the adsorbed HBsAg component with at least one further antigen from a non-HBV pathogen, to give the combination vaccine.

2. A process for preparing a combination vaccine, wherein the vaccine comprises: (i) a non-ionic surfactant, (ii) a hepatitis B virus (HBV) surface antigen (HBsAg) adsorbed onto an aluminium phosphate adjuvant, and (iii) an antigen from at least one non-HBV pathogen, and wherein the process comprises the step of combining a purified HBsAg with at least one further antigen from a non-HBV pathogen, to give the combination vaccine, wherein the HBsAg: (a) is prepared by a process in which recombinant HBsAg-expressing yeast cells are disrupted in the presence of the non-ionic surfactant, where the non-ionic surfactant is retained within the HBsAg particle, and wherein the process does not involve a step of adding the non-ionic surfactant as a separate component after HBsAg purification; and (b) is pre-adsorbed to the aluminium phosphate.

3. The process of claim 1, wherein the non-ionic surfactant includes poly(oxyethene) residues.

4. The process of claim 3, wherein the non-ionic surfactant is a polyoxyethylene sorbitan ester.

5. The process of claim 4, wherein the non-ionic surfactant is polysorbate 20.

6. The process of claim 1, wherein the non-ionic surfactant is present in the final product at ≤30 μg/ml.

7. The process of claim 1, wherein the non-ionic surfactant is present in the final product at ≤50 μg for every 100 μg of HBsAg.

8. The process of claim 1, wherein: (i) the at least one non-HBV pathogens includes *C. diphtheriae* and *C. tetani*; (ii) the antigens from these two pathogens are a diphtheria toxoid and a tetanus toxoid; and (iii) the diphtheria and tetanus toxoids are initially present in admixed form that is substantially free from polysorbate 20.

9. The process of claim 1, wherein the HBV surface antigen is non-glycosylated.

10. The process of claim 1, wherein the HBV surface antigen is in the form of particles including a lipid matrix comprising phospholipids.

11. The process of claim 1, wherein the HBV surface antigen is from HBV subtype adw2.

12. The process of claim 1, wherein the HBV surface antigen is present in the final composition at about 10 μg per dose.

13. The process of claim 1, wherein the vaccine includes a Hib conjugate, a meningococcal conjugate, and/or a pneumococcal conjugate.

14. The process of claim 1, wherein the vaccine is selected from: a 3-valent HBsAg (Hepatitis B Virus surface antigen), D (diphtheria toxoid), T (tetanus toxoid) composition; a 4-valent HBsAg, D, T, Pw (cellular pertussis antigen) composition; a 5-valent HBsAg, D, T, Pw, Hib (*Haemophilus influenzae* b capsular saccharide) composition; a 7-valent HBsAg, D, T, Pw, Hib, MenA (*Neisseria meningitidis* serogroup A), MenC (*Neisseria meningitidis* serogroup C) composition; a 8-valent HBsAg, D, T, Pw, Hib, MenA, MenC, MenW135 (*Neisseria meningitidis* serogroup W135) composition; a 8-valent HBsAg, D, T, Pw, Hib, MenA, MenC, MenY (*Neisseria meningitidis* serogroup Y) composition; a 9-valent HBsAg, D, T, Pw, Hib, MenA, MenC, MenW135, MenY composition; a 4-valent HBsAg, D, T, Pa (acellular pertussis antigen) composition; a 5-valent HBsAg, D, T, Pa, Hib composition; a 5-valent HBsAg, D, T, Pa, poliovirus composition; a 6-valent HBsAg, D, T, Pa, poliovirus, Hib composition; a 7-valent HBsAg, D, T, Pa, poliovirus, Hib, MenC composition; an 8-valent HBsAg, D, T, Pa, poliovirus, Hib, MenC, MenA composition; a 8-valent HBsAg, D, T, Pa, poliovirus, Hib, MenC, MenY composition; a 8-valent HBsAg, D, T, Pa, poliovirus, Hib, MenC, MenW135 composition; a 10-valent HBsAg, D, T, Pa, poliovirus, Hib, MenC, MenA, MenW135, MenY composition; a 2-valent HBsAg, Hib composition; and a 2-valent HBsAg, hepatitis A virus composition.

15. The process of claim 1, wherein the final composition comprises both aluminium phosphate and aluminium hydroxide adjuvants.

16. The process of claim 15, wherein the concentration of $Al^{3+}$ in the final composition is $\leq 5$ mg/ml.

17. The process of claim 1, wherein the process comprises adding a pre-mixed D-T component.

18. The process of claim 1, wherein the process comprises adding a pre-mixed D-T-Pw component.

19. The process of claim 18, wherein the pre-mixed D-T-Pw component includes both aluminium phosphate and aluminium hydroxide adjuvants.

20. The process of claim 2, wherein the non-ionic surfactant includes poly(oxyethene) residues.

21. The process of claim 20, wherein the non-ionic surfactant is a polyoxyethylene sorbitan ester.

22. The process of claim 21, wherein the non-ionic surfactant is polysorbate 20.

23. The process of claim 2, wherein the non-ionic surfactant is present in the final product at $\leq 30$ μg/ml.

24. The process of claim 2, wherein the non-ionic surfactant is present in the final product at $\leq 50$ μg for every 100 μg of HBsAg.

25. The process of claim 2, wherein: (i) the at least one non-HBV pathogens includes *C. diphtheriae* and *C. tetani*; (ii) the antigens from these two pathogens are a diphtheria toxoid and a tetanus toxoid; and (iii) the diphtheria and tetanus toxoids are initially present in admixed form that is substantially free from polysorbate 20.

26. The process of claim 2, wherein the HBV surface antigen is non-glycosylated.

27. The process of claim 2, wherein the HBV surface antigen is in the form of particles including a lipid matrix comprising phospholipids.

28. The process of claim 2, wherein the HBV surface antigen is from HBV subtype adw2.

29. The process of claim 2, wherein the HBV surface antigen is present in the final composition at about 10 μg per dose.

30. The process of claim 2, wherein the vaccine includes a Hib conjugate, a meningococcal conjugate, and/or a pneumococcal conjugate.

31. The process of claim 2, wherein the vaccine is selected from: a 3-valent HBsAg, D, T composition; a 4-valent HBsAg, D, T, Pw composition; a 5-valent HBsAg, D, T, Pw, Hib composition; a 7-valent HBsAg, D, T, Pw, Hib, MenA, MenC composition; a 8-valent HBsAg, D, T, Pw, Hib, MenA, MenC, MenW135 composition; a 8-valent HBsAg, D, T, Pw, Hib, MenA, MenC, MenY composition; a 9-valent HBsAg, D, T, Pw, Hib, MenA, MenC, MenW135, MenY composition; a 4-valent HBsAg, D, T, Pa composition; a 5-valent HBsAg, D, T, Pa, Hib composition; a 5-valent HBsAg, D, T, Pa, poliovirus composition; a 6-valent HBsAg, D, T, Pa, poliovirus, Hib composition; a 7-valent HBsAg, D, T, Pa, poliovirus, Hib, MenC composition; a 8-valent HBsAg, D, T, Pa, poliovirus, Hib, MenC, MenA composition; a 8-valent HBsAg, D, T, Pa, poliovirus, Hib, MenC, MenY composition; a 8-valent HBsAg, D, T, Pa, poliovirus, Hib, MenC, MenW135 composition; a 10-valent HBsAg, D, T, Pa, poliovirus, Hib, MenC, MenA, MenW135, MenY composition; a 2-valent HBsAg, Hib composition; and a 2-valent HBsAg, hepatitis A virus composition.

32. The process of claim 2, wherein the final composition comprises both aluminium phosphate and aluminium hydroxide adjuvant.

33. The process of claim 32, wherein the concentration of $Al^{3+}$ in the final composition is $\leq 5$ mg/ml.

34. The process of claim 2, wherein the process comprises adding a pre-mixed D-T component.

35. The process of claim 2, wherein the process comprises adding a pre-mixed D-T-Pw component.

36. The process of claim 35, wherein the pre-mixed D-T-Pw component includes both aluminium phosphate and aluminium hydroxide adjuvants.

* * * * *